United States Patent
Nakao et al.

(10) Patent No.: US 8,541,538 B2
(45) Date of Patent: Sep. 24, 2013

(54) ADSORBENT FOR THE REMOVAL OF BLOOD CELLS

(75) Inventors: Michiharu Nakao, Kanazawa (JP); Seishu Hayashi, Kanazawa (JP)

(73) Assignee: Nikkiso Co., Ltd., Tokyo (JP)

( * ) Notice: Subject to any disclaimer, the term of this patent is extended or adjusted under 35 U.S.C. 154(b) by 98 days.

(21) Appl. No.: 12/937,163

(22) PCT Filed: Apr. 17, 2009

(86) PCT No.: PCT/JP2009/058112
§ 371 (c)(1),
(2), (4) Date: Oct. 8, 2010

(87) PCT Pub. No.: WO2009/128564
PCT Pub. Date: Oct. 22, 2009

(65) Prior Publication Data
US 2011/0033704 A1    Feb. 10, 2011

(30) Foreign Application Priority Data

| Apr. 18, 2008 | (JP) | 2008-109381 |
| Jun. 12, 2008 | (JP) | 2008-154418 |
| Nov. 25, 2008 | (JP) | 2008-299521 |
| Apr. 14, 2009 | (JP) | 2009-098289 |

(51) Int. Cl.
*C08G 63/68* (2006.01)
*C08G 63/688* (2006.01)
*C08G 63/00* (2006.01)
*C08G 75/00* (2006.01)

(52) U.S. Cl.
USPC ........... 528/290; 528/272; 528/293; 528/373; 528/391

(58) Field of Classification Search
USPC .......... 528/272, 373, 391, 290, 293
See application file for complete search history.

(56) References Cited

U.S. PATENT DOCUMENTS

| 4,917,799 A | 4/1990 | Masuda et al. |
| 5,476,587 A | 12/1995 | Kuroki et al. |
| 5,707,520 A | 1/1998 | Kuroki et al. |
| 5,792,406 A | 8/1998 | Wada et al. |
| 2004/0253204 A1 | 12/2004 | Yagi et al. |
| 2008/0203024 A1 | 8/2008 | Lemke et al. |

FOREIGN PATENT DOCUMENTS

| EP | 0 169 947 A1 | 2/1986 |
| JP | A-62-243561 | 10/1987 |
| JP | A-1-121061 | 5/1989 |
| JP | A-5-168706 | 7/1993 |

(Continued)

OTHER PUBLICATIONS

Yoshida et al; Semipermeable membrane and process for preparing it; Nikkiso Co., Ltd., Japan; 1990; Chem Abstract 113: 29355.*

(Continued)

*Primary Examiner* — Duc Truong
(74) *Attorney, Agent, or Firm* — Oliff & Berridge, PLC

(57) ABSTRACT

An adsorbent for the removal of blood cells, which is formed from a hydrophobic polymer resin and has a surface center line average roughness of 5 to 100 nm. The hydrophobic polymer resin is preferably a polyarylate resin (PAR), polyethersulfone resin (PES), polysulfone resin (PSF), or a polymer alloy consisting of two or more of these resins. The adsorbent for the removal of blood cells can take the form of beads, hollow fibers, or solid fibers.

6 Claims, 11 Drawing Sheets

(56) References Cited

FOREIGN PATENT DOCUMENTS

| | | |
|---|---|---|
| JP | U-5-96033 | 12/1993 |
| JP | U-6-27092 | 4/1994 |
| JP | A-7-124255 | 5/1995 |
| JP | A-9-277190 | 10/1997 |
| JP | A-2005-65711 | 3/2005 |
| JP | B2-3699480 | 9/2005 |
| JP | A-2006-77136 | 3/2006 |
| JP | A-2006-181522 | 7/2006 |
| JP | A-2006-246963 | 9/2006 |
| WO | WO 03/011924 A1 | 2/2003 |
| WO | WO 2007/057065 A1 | 5/2007 |

OTHER PUBLICATIONS

Danese et al., "Platelets in Inflammatory Bowel Disease: Clinical, Pathogenic, and Therapeutic Implications," American Journal of Gastroenterology, 2004, pp. 938-945.

Pitchford, "Novel uses for anti-platelet agents as anti-inflammatory drugs," British Journal of Pharmacology, 2007, pp. 987-1002, vol. 152.

Fukunaga et al., "Selective Platelet Removal as a Novel Therapy for Refractory Crohn's Disease," Jpn J Apheresis, 2007, pp. 266-271, vol. 26—No. 2.

Miura et al., "Comparison of Adverse Events between Adsorption-Type Blood Purifier Adacolumn and Celisorba Ex," Journal of the Japan Association for Clinical Engineering Technologists, 2003, pp. 30-31, No. 19 (with translation).

Japanese Office Action dated Jun. 16, 2009 issued in Japanese Patent Application No. 2008-109381 (with translation).

Japanese Office Action dated Dec. 1, 2009 issued in Japanese Patent Application No. 2008-109381 (with translation).

International Search Report mailed on Jun. 30, 2009 issued in International Patent Application No. PCT/JP2009/058112 (with translation).

Extended European Search Report issued in European Application No. 09731790.3 dated May 6, 2011.

Canadian Office Action dated Sep. 27, 2012 from Canadian Patent Application No. 2,720,665.

\* cited by examiner

ADSORBENT FOR THE REMOVAL OF BLOOD CELLS

TECHNICAL FIELD

The present invention relates to an adsorbent for the removal of blood cells, which is used for removing the white blood cells and blood platelets contained within blood.

BACKGROUND ART

In recent years, white blood cell adsorption devices have started to be used widely as treatment devices for inflammatory bowel disease (IBD) and rheumatoid arthritis (RA). White blood cell adsorption devices use the principles of adsorption and filtration to directly remove the white blood cells, which can cause inflammation, from the blood, and have been shown to have a therapeutic effect. The main advantage of medical treatments using a white blood cells adsorption device is that, unlike treatments using drugs, side-effects are minimal. For the white blood cell adsorption devices in current use, methods that employ a carrier having a specified surface roughness and methods that employ a filter composed of ultra-fine polymer fibers have been proposed.

For example, Patent Document 1 discloses a carrier for adsorbing granulocytes that has an irregular surface for which the center line average roughness Ra is within a range from 0.2 μm to 100 μm and the average spacing Sm between irregularities is within a range from 5 μm to 200 μm.

Further, Patent Document 2 proposes a method of producing porous beads in which at least two polymers each having a number average molecular weight of at least 10,000 but having different coagulation values are dissolved in a solvent that exhibits favorable compatibility with each polymer, and the resulting polymer solution is then added dropwise to a coagulant containing a non-solvent, thereby causing coagulation and producing porous beads.

Moreover, Patent Document 3 discloses a technique in which by aligning the fibers of an organic polymer with a high degree of regularity, namely in a substantially parallel arrangement, and then passing blood between these fibers, the white blood cells can be captured on the surface of the fibers while those problems that have proven difficult to prevent using filters formed from nonwoven fabrics or the like, such as the destruction of blood cells and the coagulation of the blood, can be overcome.

These methods have been proposed for removing mainly the white blood cells such as granulocytes and lymphocytes from the blood of patients suffering from cancer or immune system abnormalities. However, recent research has made it clear that particularly in the case of inflammatory diseases such as autoimmune disease, it is not only the white blood cells, but also the platelets within the blood, that act as inflammatory cells.

PRIOR ART

Patent Document
  PATENT DOCUMENT 1: JP 05-168706 A
  PATENT DOCUMENT 2: JP 62-243561 A
  PATENT DOCUMENT 3: EP 1,931,404

DISCLOSURE OF INVENTION

Problems to be Solved by the Invention

The present invention proposes an adsorbent for the removal of blood cells that suffers minimal problems such as in-circuit coagulation during blood flow, and enables efficient removal of white blood cells and platelets.

Means for Solving the Problems

One aspect of the present invention relates to an adsorbent for removing blood cells. The adsorbent for removing blood cells is formed from a hydrophobic polymer resin, and has a surface center line average roughness (Ra) of 5 to 100 nm.

By using the adsorbent for removing blood cells of this aspect, white blood cells and platelets can be removed efficiently from the blood, while the occurrence of blood coagulation during passage of the blood through a column or circuit is suppressed.

In the aspect described above, the hydrophobic polymer resin may be a polyarylate resin having a repeating unit represented by chemical formula (1) shown below.

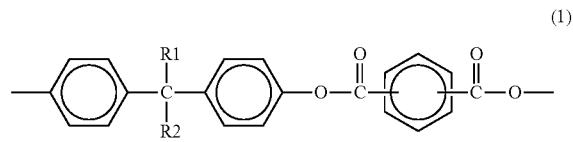

(1)

In chemical formula (1), each of R1 and R2 represents a lower alkyl group of 1 to 5 carbon atoms, and R1 and R2 may be the same or different.

In the aspect described above, the hydrophobic polymer resin may be a polyethersulfone resin having a repeating unit represented by chemical formula (2) or chemical formula (3) shown below.

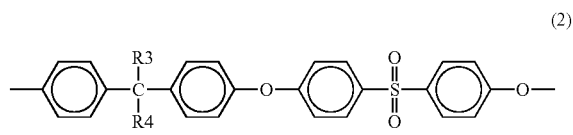

(2)

In chemical formula (2), each of R3 and R4 represents a lower alkyl group of 1 to 5 carbon atoms, and R3 and R4 may be the same or different.

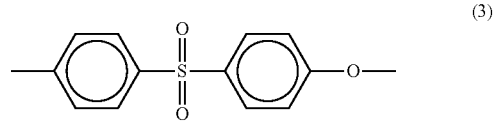

(3)

In the aspect described above, the hydrophobic polymer resin may include a polyarylate resin having a repeating unit represented by chemical formula (1) shown above, and a polyethersulfone resin having a repeating unit represented by chemical formula (2) or chemical formula (3) shown above.

The adsorbent for removing blood cells according to the aspect described above may be in the form of beads. Further, the adsorbent for removing blood cells according to the aspect described above may also exist in the form of hollow thread-like fibers or solid thread-like fibers. Furthermore, the adsorbent for removing blood cells according to the aspect described above may be used for the removal of white blood cells and platelets from blood.

Appropriate combinations of each of the elements described above are also deemed to be included within the scope of the invention for which patent protection is sought on the basis of the present description.

ADVANTAGES OF THE INVENTION

According to the present invention, white blood cells and platelets can be removed efficiently from blood with minimal problems such as in-circuit coagulation during blood flow.

BEST MODE FOR CARRYING OUT THE INVENTION

[First Embodiment]

Figure 1:
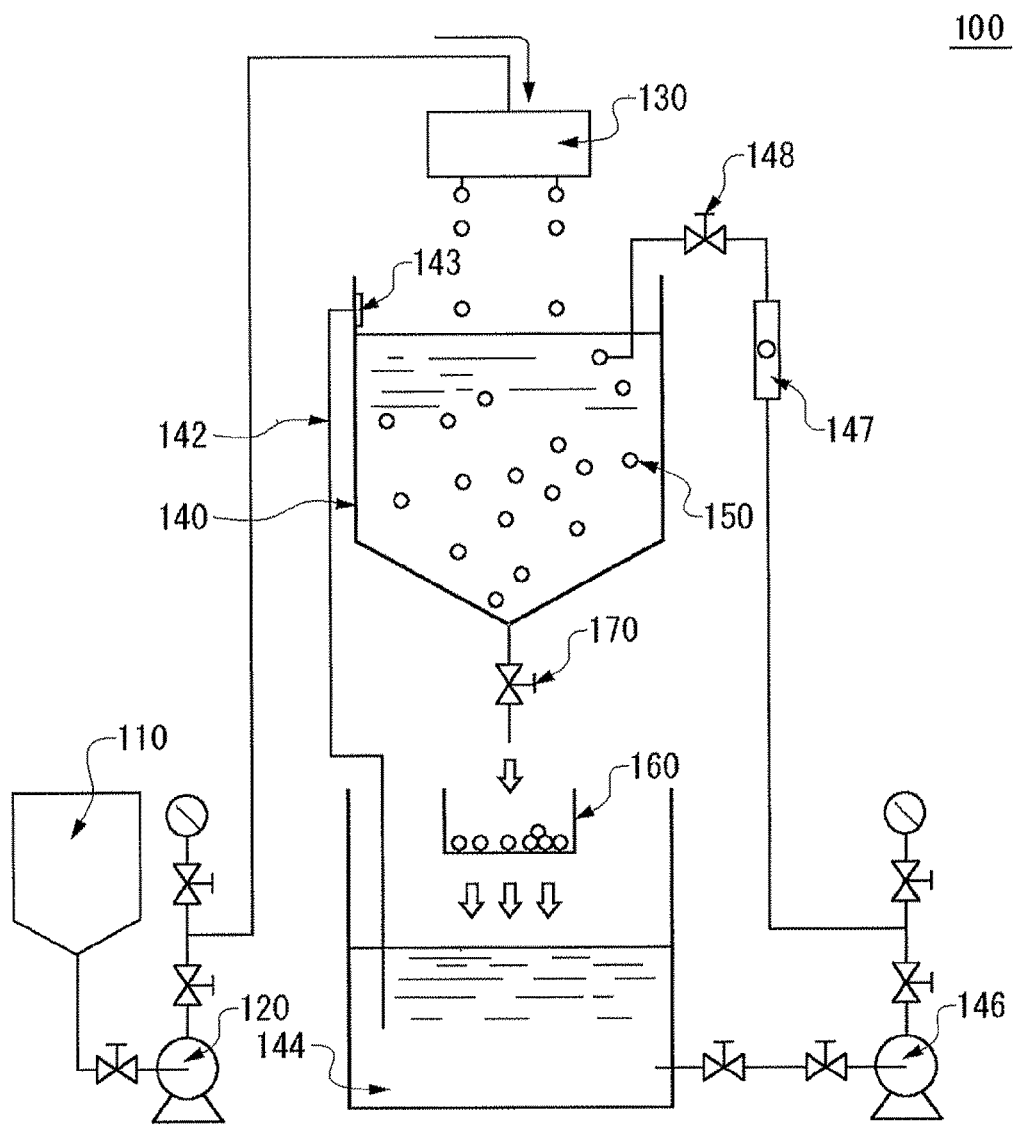
FIG. 1 is a schematic illustration of a porous beads production apparatus used in the production of beads for removing blood cells.

An adsorbent for removing blood cells according to this embodiment is formed from a hydrophobic polymer resin, and has a surface center line average roughness (Ra) of 5 to 100 nm.

By ensuring that the material at the surface of the adsorbent is a hydrophobic polymer resin, the resulting hydrophobic interactions are able to improve the adsorption of white blood cells such as granulocytes and lymphocytes, and platelets.

The hydrophobic polymer resin is preferably a polyarylate resin (PAR), polyethersulfone resin (PBS), polysulfone resin (PSF), or a polymer alloy of these resins.

A polyarylate resin is a resin having a repeating unit represented by chemical formula (1) shown below. The number average molecular weight of the polyarylate resin is preferably within a range from 20,000 to 30,000. If the number average molecular weight of the polyarylate resin exceeds 30,000, then the surface roughness tends to become too great, and forming an appropriate level of surface roughness becomes difficult. In contrast, if the number average molecular weight of the polyarylate resin is less than 20,000, then the strength of the adsorbent for removing blood cells tends to deteriorate, and the production yield of the adsorbent for removing blood cells worsens.

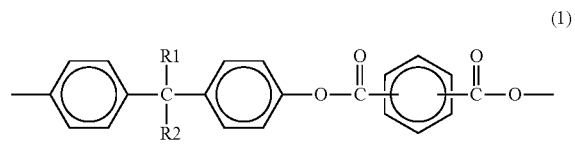

In chemical formula (1), each of R1 and R2 represents a lower alkyl group of 1 to 5 carbon atoms, and R1 and R2 may be the same or different. Specific examples of R1 and R2 include a methyl group, ethyl group, propyl group, butyl group and pentyl group. R1 and R2 are preferably methyl groups.

There are no particular limitations on the polyarylate resin, provided that the repeating unit represented by chemical formula (1) represents the main repeating unit, and the polyarylate resin may also include other repeating units, provided they do not impair the effects of the present invention.

A polyethersulfone resin is a resin having a repeating unit represented by chemical formula (2) or chemical formula (3) shown below. The number average molecular weight of the polyethersulfone resin is preferably within a range from 15,000 to 30,000. If the number average molecular weight of the polyethersulfone resin exceeds 30,000, then the surface roughness tends to become too great, and forming an appropriate level of surface roughness becomes difficult. In contrast, if the number average molecular weight of the polyethersulfone resin is less than 15,000, then the strength of the adsorbent for removing blood cells tends to deteriorate, and the production yield of the adsorbent for removing blood cells worsens.

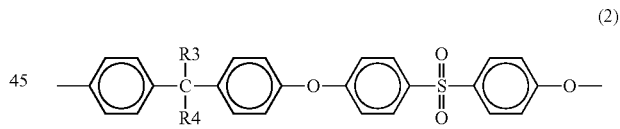

In chemical formula (2), each of R3 and R4 represents a lower alkyl group of 1 to 5 carbon atoms, and R3 and R4 may be the same or different. Specific examples of R3 and R4 include a methyl group, ethyl group, propyl group, butyl group and pentyl group. R3 and R4 are preferably methyl groups.

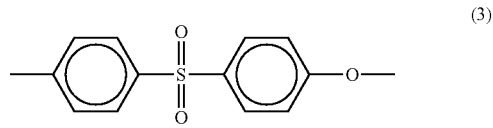

Ensuring that the surface Ra value of the adsorbent for removing blood cells is within a range from 5 to 100 nm enables a further improvement in the adsorption of white blood cells and platelets. Achieving a surface Ra value of less than 5 nm for the adsorbent for removing blood cells is problematic from a production perspective. In contrast, if the surface Ra value of the adsorbent for removing blood cells exceeds 100 nm, then the contribution of the adsorbent to the adsorption of platelets (size: 2 to 4 μm) tends to decrease, and production of the adsorbent by a coagulation method becomes problematic. The surface Ra value of the adsorbent for removing blood cells can be measured using an AFM (atomic force microscope). The AFM measurement region is typically 10 μm×10 μm.

The adsorbent for removing blood cells according to this embodiment is ideal for use within a treatment for removing white blood cells and platelets. Specifically, by packing the adsorbent for removing blood cells according to the embodiment inside a column, and then passing blood through the column, white blood cells and platelets can be removed from the blood. In this case, by packing the adsorbent for removing blood cells inside the column, passages are formed between adjacent particles of the adsorbent for removing blood cells, thereby ensuring a ready flow of blood and suppressing the occurrence of blood coagulation. Moreover, the white blood cells and platelets can be removed simply and efficiently from the blood without requiring the use of a complex apparatus.

The adsorbent for removing blood cells preferably exists in the form of beads or fibers such as hollow thread-like fibers or solid thread-like fibers.

In those cases where the adsorbent for removing blood cells exists in the form of beads (hereafter referred to as "beads for removing blood cells"), the diameter of the beads is preferably within a range from 0.5 to 5 mm. Forming the adsorbent for removing blood cells as beads yields the effects described below.

(1) Compared with LCAP (leukocytapheresis) using an ultra-fine fibrous nonwoven fabric, pressure loss within the column is minimal and problems such as coagulation are relatively minor, even in those cases where the viscosity of the blood from the patient is high, and there is a high risk of problems such as coagulation within the column.
(2) Unlike LCAP, lymphocytes are not removed, meaning the danger of removing immunity-related memory cells is reduced.
(3) Compared with GCAP (granulocytapheresis), which also uses a beads-type adsorbent, a larger amount of platelets can be removed, and therefore inflammation symptoms derived from platelets can be more effectively suppressed.
(4) Because treatment can be performed simply by passing the whole blood through a disposable column, a treatment can be provided that offers simplicity and a high level of safety.
(5) Because expensive equipment such as a centrifuge is not required, the treatment can be performed inexpensively.

Furthermore, in those cases where the adsorbent for removing blood cells exists in the form of hollow fibers or solid fibers (hereafter referred to as "hollow fibers for removing blood cells" and "solid fibers for removing blood cells" respectively), the fibers preferably have an external diameter of 0.1 to 5 mm. Forming the adsorbent for removing blood cells as hollow fibers or solid fibers yields the effects described below besides the effects listed above.

(1) Compared with LCAP using an ultra-fine fibrous nonwoven fabric, forming the adsorbent for removing blood cells as hollow fibers or solid fibers enables treatment to be performed with comparatively few problems, even in those cases where the viscosity of the blood from the patient is high, and there is a high risk of problems such as coagulation within the column.
(2) By using hollow fibers or solid fibers, the production efficiency of the adsorbent for removing blood cells can be improved, thereby reducing the production costs.

[Method of Producing Beads for Removing Blood Cells]

A method of producing beads for removing blood cells according to an embodiment of the present invention is described below. First, the hydrophobic polymer resin is dissolved in N-methyl-2-pyrrolidone (hereafter referred to as NMP) to prepare a polymer solution (the stock solution). A mixture prepared by mixing NMP with water is used as the coagulant. The polymer solution is added dropwise to the coagulant bath from a nozzle having an internal diameter of 0.25 mm and from a height approximately 10 cm above the liquid surface within the tank (see FIG. 1). Following thorough coagulation within the coagulant, the resulting beads are washed with distilled water to obtain the beads for removing blood cells.

FIG. 1 is a schematic illustration of a blood cells removal beads production apparatus 100 used in the production of beads for removing blood cells. The stock solution stored in a stock solution tank 110 is supplied to a nozzle 130 using a pump 120. The stock solution supplied to the nozzle 130 drips down from the nozzle 130. A coagulant bath 140 containing the coagulant is provided beneath the nozzle 130. The coagulant bath 140 may also be provided with a rotor (not shown in the figure) for generating a spiral-like flow within the coagulant.

An overflow pipe 142 is fitted to the upper portion of the coagulant bath 140. When the liquid level of the coagulant contained within the coagulant bath 140 reaches the port where the overflow pipe 142 is attached, the overflowing coagulant flows down through the overflow pipe 142 and is collected in a coagulant collection tank 144. A mesh 143 having a mesh size that is finer than the diameter of the beads 150 for removing blood cells produced within the coagulant bath 140 is preferably provided at the port where the overflow pipe 142 is attached. This prevents beads 150 for removing blood cells from contaminating the coagulant collection tank 144 as foreign matter.

The coagulant collected in the coagulant collection tank 144 is pumped back up using a coagulant circulation pump 146 and returned to the coagulant bath 140. The amount of the coagulant supplied from the coagulant collection tank 144 to the coagulant bath 140 is detected by a flow rate meter 147, and an appropriate amount of the coagulant is supplied to the coagulant bath 140 using a coagulant supply volume regulating valve 148. By circulating the overflowed coagulant in this manner, the coagulant can be used more efficiently, and the production costs for the beads 150 for removing blood cells can be kept to a minimum.

The stock solution that is dripped into the coagulant bath 140 from the nozzle 130 solidifies in a spherical form within the coagulant, thus forming the beads 150 for removing blood cells. By adding the stock solution dropwise to the coagulant, the spherical beads 150 for removing blood cells can be obtained in a stable manner with good yield.

The solidified beads 150 for removing blood cells are discharged from the bottom of the coagulant bath 140, and collected on a screen 160 having a mesh size that is finer than the diameter of the beads 150 for removing blood cells. The volume of the coagulant containing the beads 150 for removing blood cells discharged from the coagulant bath 140 is regulated appropriately using a coagulant discharge volume regulating valve 170. The coagulant discharged from the coagulant bath 140 together with the beads 150 for removing blood cells is collected in the coagulant collection tank 144 and reused.

[Method of Producing Hollow Fibers for Removing Blood Cells]

A method of producing hollow fibers for removing blood cells according to an embodiment of the present invention is described below. First, the hydrophobic polymer resin is dissolved in an organic solvent to prepare a spinning stock solution. There are no particular limitations on the organic solvent, provided it acts as a good solvent with respect to the hydrophobic polymer resin, and specific examples include tetrahydrofuran, dioxane, dimethylformamide, dimethylacetamide and NMP. Of these, NMP is preferred as the organic solvent.

By using a double nozzle to extrude the spinning stock solution together with an internal coagulant (an organic solvent containing water) and dropping the solution into an external coagulant (an organic solvent containing water), hollow fibers for removing blood cells can be produced. The temperature during spinning of these hollow fibers for removing blood cells is preferably within a range from approximately 5 to 15° C. By setting the spinning temperature within this range, the stability of the spinning stock solution is improved, thereby inhibiting phase separation and the like. The ratio between the concentrations of the internal coagulant (the core liquid) and the external coagulant is preferably within a range from 0.6 to 1.6.

[Method of Producing Solid Fibers for Removing Blood Cells]

A method of producing solid fibers for removing blood cells according to an embodiment of the present invention is described below. First, the hydrophobic polymer resin is dissolved in an organic solvent to prepare a spinning stock solution. There are no particular limitations on the organic solvent, provided it acts as a good solvent with respect to the hydrophobic polymer resin, and specific examples include tetrahydrofuran, dioxane, dimethylformamide, dimethylacetamide and NMP. Of these, NMP is preferred as the organic solvent.

By using a typical nozzle (orifice) to drop the spinning stock solution into a coagulant (an organic solvent containing water), solid fibers for removing blood cells can be produced. The temperature during spinning of these solid fibers for removing blood cells is preferably within a range from approximately 5 to 15° C. By setting the spinning temperature within this range, the stability of the spinning stock solution is improved, thereby inhibiting phase separation and the like.

[Second Embodiment]

Figure 6A:
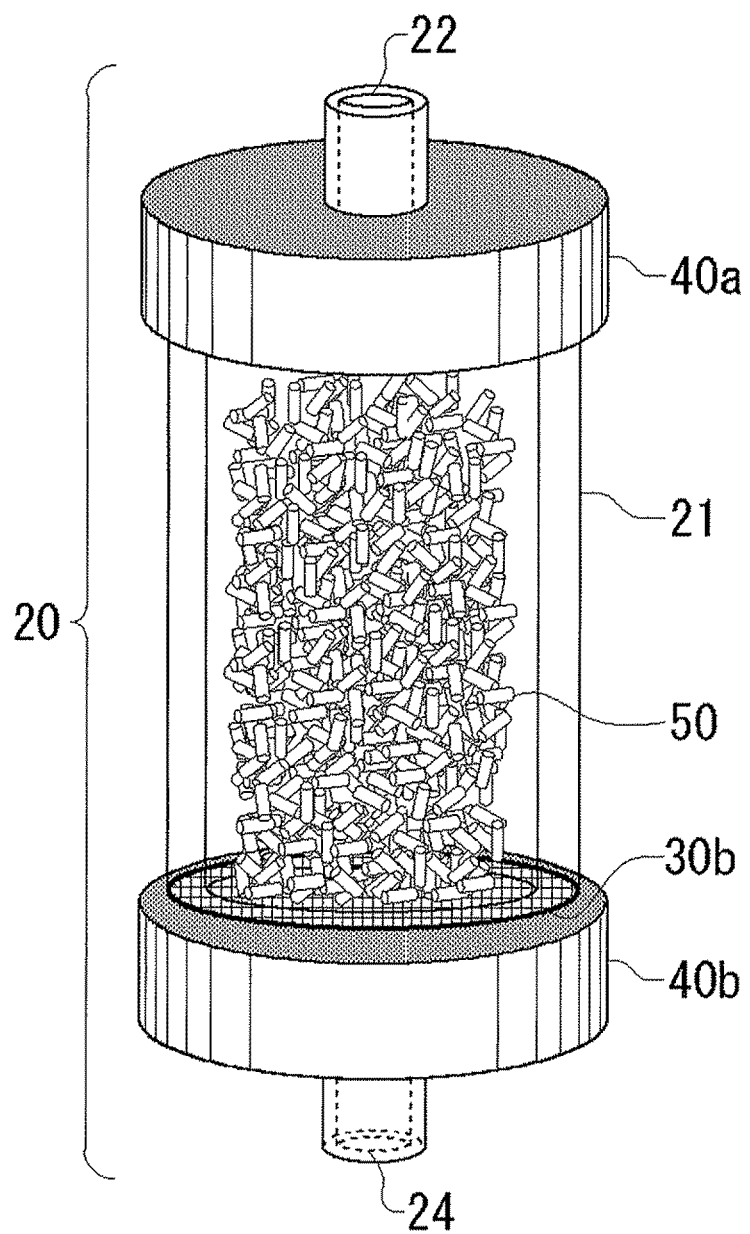
FIG. 6A is a perspective view of the structure of a blood cells removal module according to an embodiment.
Figure 6B:
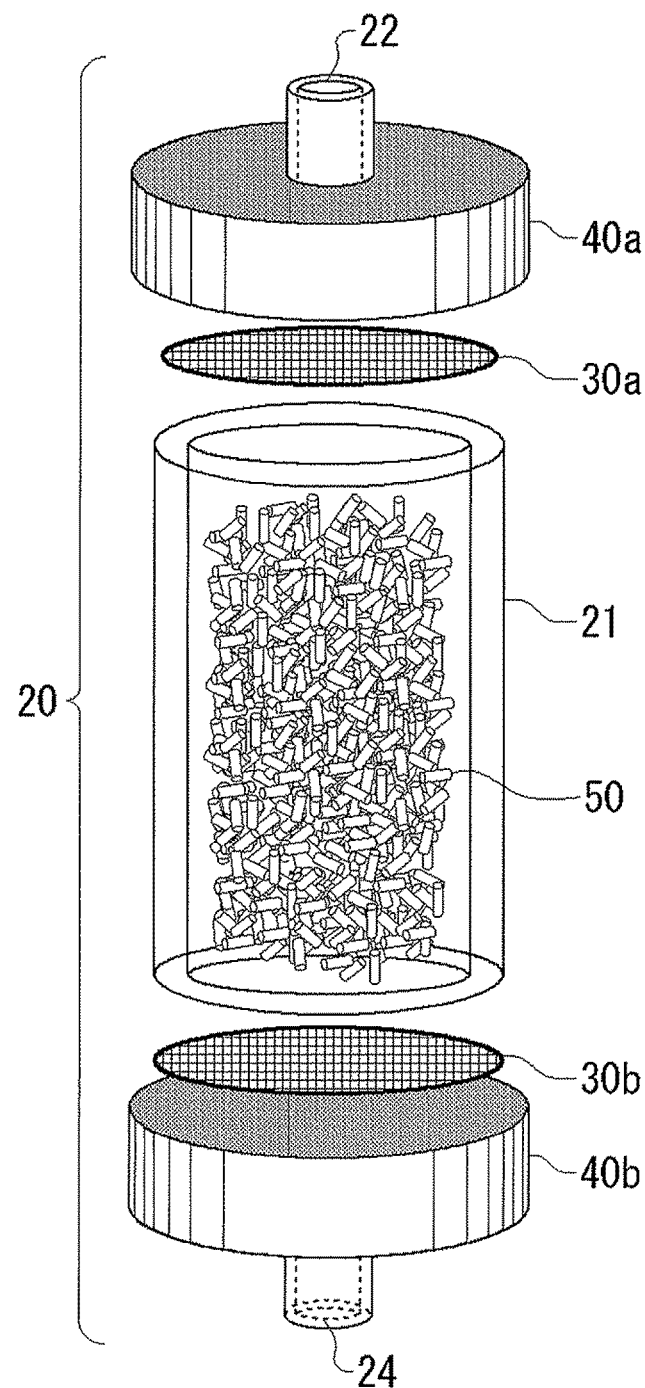
FIG. 6B is an exploded perspective view of the structure of a blood cells removal module according to an embodiment.

An embodiment of the present invention is described below with reference to the drawings. FIG. 6A is a perspective view of the structure of a blood cells removal module according to the embodiment. FIG. 6B is an exploded perspective view of the structure of the blood cells removal module according to the embodiment. The blood cells removal module 10 comprises a casing 20 and an adsorbent 50 for removing blood cells.

The casing 20 comprises a casing main body 21, a pair of meshes 30a and 30b, and a pair of headers 40a and 40b. The casing main body 21 is a circular cylindrical member produced from a polycarbonate. However, the material for the casing main body 21 is not limited to polycarbonate, and other known resin materials, metal materials or composite materials may also be used.

The pair of polyester meshes 30a and 30b are attached to the two open ends of the casing main body 21. These meshes 30a and 30b have a mesh size that is finer than the external diameter of the adsorbent 50 for removing blood cells described below, meaning the meshes retain the adsorbent 50 for removing blood cells inside the casing. The material for the meshes 30a and 30b is not limited to polyester, and other known resin materials, metal materials or composite materials may also be used.

A header 40a is fitted to one of the open ends of the casing main body 21 with the aforementioned mesh 30a sandwiched therebetween. An inlet 22 that functions as the blood introduction point is provided in the header 40a. Further, a header 40b is fitted to the other open end of the casing main body 21 with the aforementioned mesh 30b sandwiched therebetween. An outlet 24 that functions as the blood discharge point is provided in the header 40b. The two open ends of the casing main body 21 are sealed by the header 40a and the header 40b. In order to achieve more reliable sealing, sealing members such as O-rings may be provided between the header 40a and the casing main body 21 and between the header 40b and the casing main body 21.

The inside of the casing main body 21 between the pair of meshes 30a and 30b houses the adsorbent 50 for removing blood cells. The adsorbent 50 for removing blood cells is arranged randomly inside the casing main body 21, namely in an irregular and unrestrained manner. The adsorbent 50 for removing blood cells is composed of short hollow fibers or short solid fibers, wherein the length of the fibers is preferably within a range from 1 to 60%, and more preferably 18 to 56%, of the internal diameter of the casing main body 21. Setting the length of the adsorbent 50 for removing blood cells to a value of less than 1% of the internal diameter of the casing main body 21 tends to cause a deterioration in productivity. In contrast, if the length of the adsorbent 50 for removing blood cells exceeds 60% of the internal diameter of the casing main body 21, then the fibers of the adsorbent 50 for removing blood cells tend to interfere with each other inside the casing main body 21, thereby restricting free movement of the individual fibers of the adsorbent 50 for removing blood cells, and if air becomes trapped by a fiber, then removal of that air from the casing becomes difficult. In other words, because air removal becomes more difficult, the residual air is more likely to cause coagulation within the blood. Further, the contact surface area between the adsorbent for removing blood cells and the blood decreases, which may result in a reduction in the adsorption performance.

The filling rate of the adsorbent 50 for removing blood cells relative to the volume of the casing main body 21 is preferably within a range from 20 to 60%. Ensuring that the filling rate of the adsorbent 50 for removing blood cells is at least 20% reduces the blood volume required for blood purification, thereby lightening the impact on the patient. In contrast, if the filling rate of the adsorbent 50 for removing blood cells exceeds 60%, then the filling process becomes difficult, and may cause a reduction in the operating efficiency.

The adsorbent 50 for removing blood cells is formed from a hydrophobic polymer resin. Consequently, the surface of the adsorbent 50 for removing blood cells is hydrophobic, and the resulting hydrophobic interactions are able to efficiently remove not only the granulocytes that function as inflammatory cells, but also the platelets. Moreover, inflammatory symptoms caused by autoimmune disease can be suppressed with minimal side-effects.

The same resins as those described above for the first embodiment may be used as the hydrophobic polymer resin. Accordingly, description of the resin is omitted here.

Ensuring that the surface Ra value of the adsorbent for removing blood cells is within a range from 5 to 100 nm enables a further improvement in the adsorption of white blood cells and platelets. As mentioned above, achieving a surface Ra value of less than 5 nm for the adsorbent for removing blood cells is problematic from a production perspective. In contrast, if the surface Ra value of the adsorbent for removing blood cells exceeds 100 nm, then the contribution of the adsorbent to the adsorption of platelets (size: 2 to 4 μm) tends to decrease. The surface Ra value of the adsorbent for removing blood cells can be measured using an AFM (atomic force microscope). The AFM measurement region is typically 10 μm×10 μm.

By employing the blood cells removal module described above, stimulation of the coagulation system is minimal, so that when the module is used as a blood purification column during a medical treatment, coagulation of the blood during the treatment is unlikely. Further, air removal during priming (blood introduction) can be performed favorably.

Furthermore, because the adsorbent for removing blood cells can be produced with a high degree of production efficiency simply by cutting a hollow or solid fiber that is able to be produced in a continuous manner, the cost of the blood cells removal module can be reduced.

[Third Embodiment]

A blood cells removal module and a method of producing the blood cells removal module according to another embodiment of the present invention are described below. Those structural members that are the same as those described above in the first and second embodiments are referred to using the same labels, and the description of these members is omitted.

Figure 7:
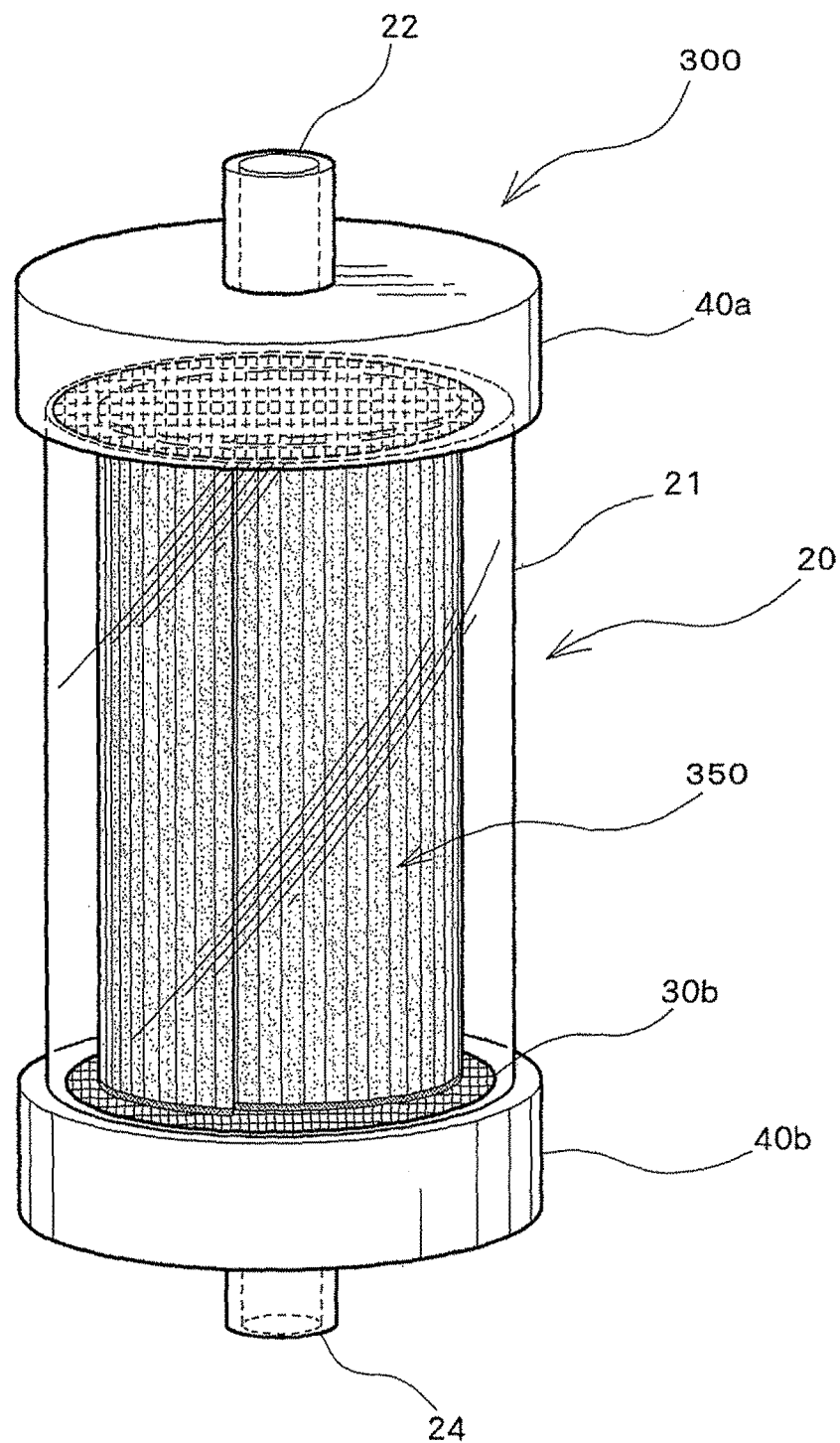
FIG. 7 is a perspective view of one example of the structure of a blood cells removal module according to an embodiment of the present invention.
Figure 8:
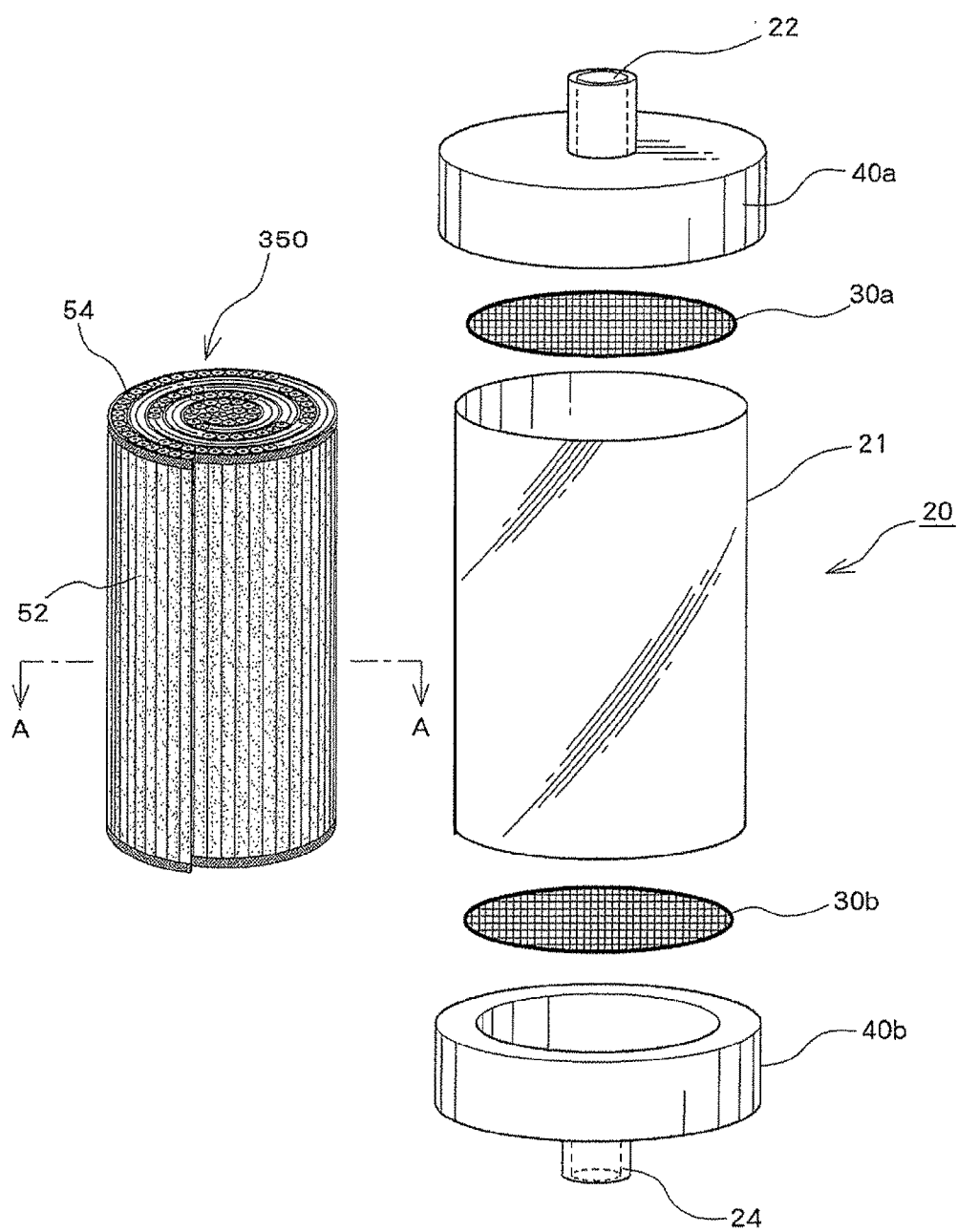
FIG. 8 is an exploded perspective view of one example of a blood cells removal module according to an embodiment of the present invention.

As illustrated in FIG. 7 and FIG. 8, the blood cells removal module 300 according to this embodiment has a cylindrical adsorbent 350 for removing blood cells contained inside a casing 20. The casing 20 comprises a casing main body 21, a pair of headers 40a and 40b fitted with a blood inlet 22 and blood outlet 24 respectively, and where necessary a pair of meshes 30a and 30b.

Figure 9:
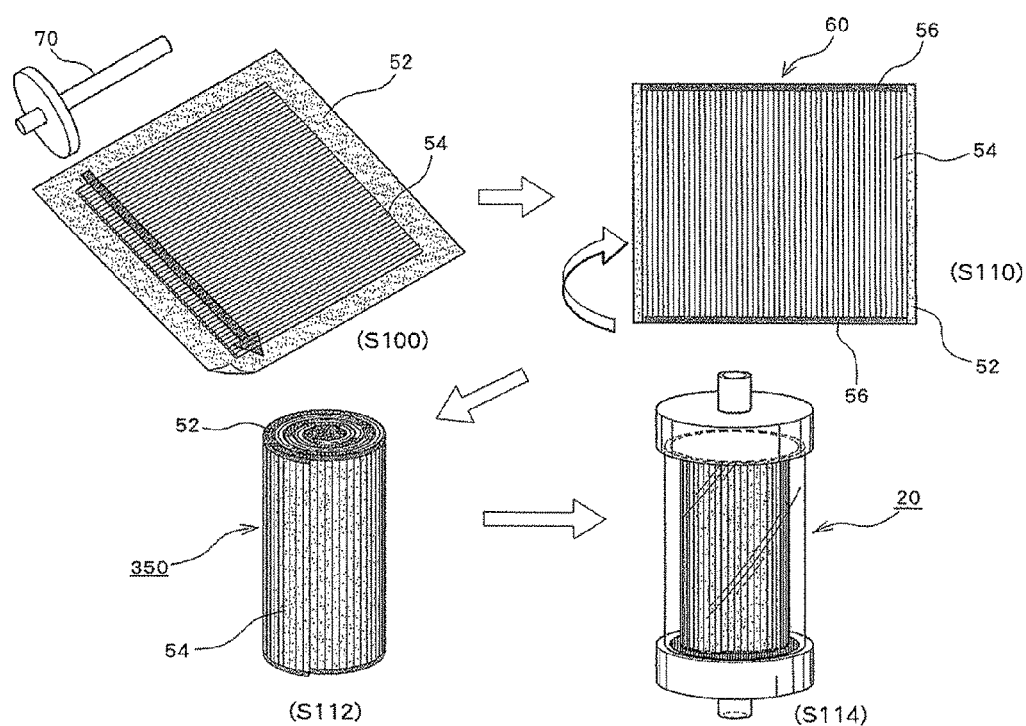
FIG. 9 is a diagram describing one example of a method of producing a blood cells removal module according to an embodiment of the present invention.
Figure 10:
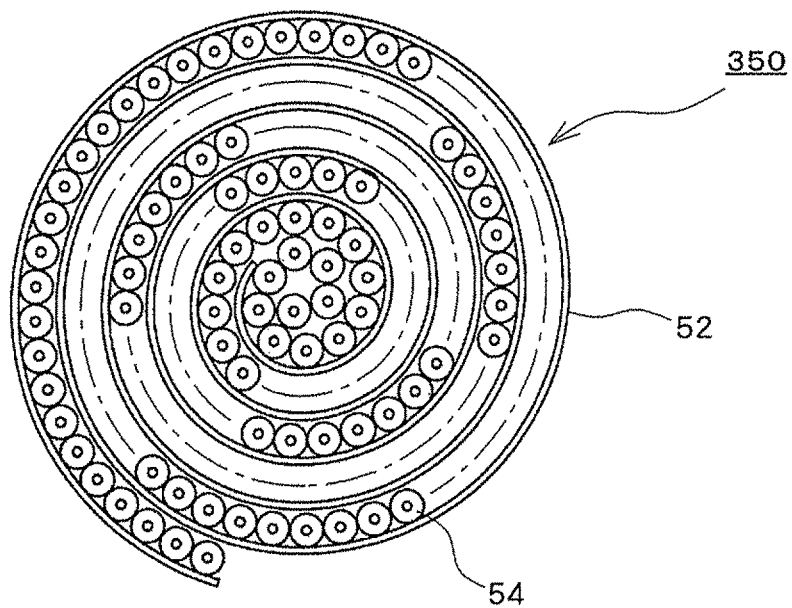
FIG. 10 is a diagram describing the structure of a cylindrical adsorbent for removing blood cells according to an embodiment of the present invention, and illustrates one example of the cross-section along the line A-A in FIG. 8.

As illustrated in FIG. 8, FIG. 9 and FIG. 10, the cylindrical adsorbent 350 for removing blood cells is formed by rolling an integrated blood cells removal adsorbent-containing mesh-like fabric 60, in which an adsorbent 54 for removing blood cells that is formed from a plurality of aligned hollow fibers or solid fibers is secured at both ends to a mesh-like fabric 52 that is permeable to blood, along the direction of alignment of the adsorbent 54 for removing blood cells. When securing both ends of the adsorbent 54 for removing blood cells to the mesh-like fabric 52 that is permeable to blood, an adhesive may be used to secure the two members, or both ends of the adsorbent 54 for removing blood cells may be secured by fusing the ends to the mesh-like fabric 52 that is permeable to blood. In those cases where the adsorbent 54 for removing blood cells is composed of hollow fibers, using fusion (and particularly thermal fusion) to secure the fibers enables the hollows at both ends of the adsorbent for removing blood cells to be sealed more easily than a securing process that uses an adhesive. As a result, when incorporated within the blood cells removal module 300, penetration of blood components into the interior of the hollow fibers can be suppressed, thereby preventing blood retention within the fibers.

A method of producing the cylindrical adsorbent 350 for removing blood cells and the blood cells removal module according to this embodiment is described with reference to FIG. 9. This description focuses on an example where fusion is used as the method of securing both ends of the adsorbent 54 for removing blood cells to the mesh-like fabric 52 that is permeable to blood. As illustrated in FIG. 9, the adsorbent 54 for removing blood cells that is formed from a plurality of aligned hollow fibers or solid fibers is first arranged on top of the mesh-like fabric 52, which is formed from a mesh or the like and is permeable to blood. Next, a fusion device 70 is used to fuse and secure both ends of the adsorbent 54 for removing blood cells to the mesh-like fabric 52, thereby sealing the ends of the adsorbent 54 for removing blood cells (S100) and forming the integrated blood cells removal adsorbent-containing mesh-like fabric 60. This fusion device 70 may use either thermal fusion or ultrasonic fusion. As described below, the adsorbent 54 for removing blood cells is formed from a resin, and the mesh-like fabric 52 is also formed from a resin. Accordingly, by using the fusion device 70, both ends of the adsorbent 54 for removing blood cells can be secured to the mesh-like fabric 52 without using an adhesive, and both ends of the adsorbent 54 for removing blood cells can be sealed. The end portions outside the fused portions 56 of the integrated blood cells removal adsorbent-containing mesh-like fabric 60 may be either left or cut off and removed. Subsequently, the obtained integrated blood cells removal adsorbent-containing mesh-like fabric 60 is rolled along the direction of alignment of the adsorbent 54 for removing blood cells, as indicated by the white arrow in the figure (S110), thus forming the cylindrical adsorbent 350 for removing blood cells, which is composed of a bundle of the fibers of the adsorbent 54 for removing blood cells with the mesh-like fabric 52 interposed therebetween as a spacer (S112). The blood cells removal module according to the present embodiment is then produced by housing the cylindrical adsorbent 350 for removing blood cells inside the casing 20. Instead of employing the fusion securing method described above, an adhesive may be used for the securing process, with the ends of the adsorbent 54 for removing blood cells then sealed with an adhesive if required.

In the produced cylindrical adsorbent 350 for removing blood cells, the mesh-like fabric 52 functions as a spacer for the adsorbent 54 for removing blood cells formed from the plurality of hollow fibers or solid fibers, and as a result, the distance between individual fibers of the adsorbent 54 for removing blood cells housed inside the casing 20 is substantially uniform throughout the blood cells removal module, and this distance is formed with an appropriate spacing. Accordingly, stagnation of the blood flow through the blood cells removal module is suppressed, the blood cells adsorption efficiency of the blood cells removal module of the present embodiment improves, and because unlike conventional modules, the ends of the adsorbent for removing blood cells composed of fibers need not necessarily be secured using a mesh, the number of components in the module can be reduced and the production process can be simplified.

Furthermore, in those cases where the adsorbent 54 for removing blood cells is composed of hollow fibers, because the hollows at both end faces of the thermally fused adsorbent 54 for removing blood cells are sealed, penetration of the blood into the interior of the hollow fibers of the adsorbent 54 for removing blood cells during blood cells removal, resulting in blood retention, can be suppressed.

Figure 11:
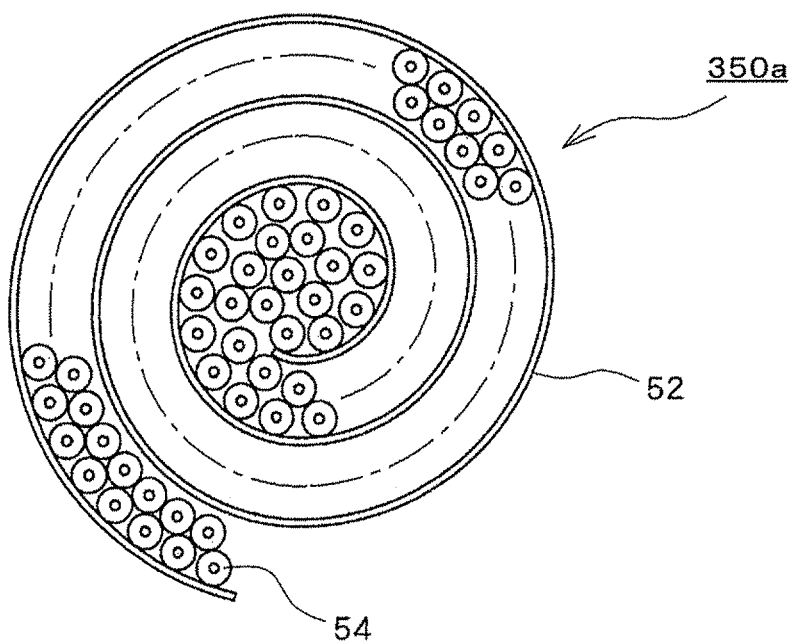
FIG. 11 is a diagram describing the structure of a cylindrical adsorbent for removing blood cells according to an embodiment of the present invention, and illustrates another example of the cross-section along the line A-A in FIG. 8.

The cylindrical adsorbent 350 for removing blood cells according to this embodiment may be formed by arranging either one layer or a plurality of layers of the adsorbent 54 for removing blood cells on top of the mesh-like fabric 52, fusing both ends of the adsorbent 54 for removing blood cells, and then rolling the fabric. Examples of the structure of the cylindrical adsorbent 350 for removing blood cells according to this embodiment are described below, using the cross-sectional views along the line A-A in FIG. 8 illustrated in FIG. 10 and FIG. 11. FIG. 10 illustrates a cylindrical adsorbent 350 for removing blood cells that is formed by aligning and then fusing one layer of the adsorbent 54 for removing blood cells on top of the mesh-like fabric 52, and then rolling the fabric along the direction of alignment of the adsorbent 54 for removing blood cells. Further, FIG. 11 illustrates a cylindrical adsorbent 350a for removing blood cells that is formed by aligning and then fusing two layers of the adsorbent 54 for removing blood cells on top of the mesh-like fabric 52, and then rolling the fabric along the direction of alignment of the adsorbent 54 for removing blood cells. A decision as to how many layers of the adsorbent 54 for removing blood cells should be aligned and then fused on top of the mesh-like fabric 52 can be made on the basis of factors such as the diameter and length of the fibers of the adsorbent 54 for removing blood cells, and the viscosity of the blood to be passed through the adsorbent.

Next is a description of specifics relating to the adsorbent 54 for removing blood cells formed from hollow fibers or solid fibers that is used in the blood cells removal module according to the present embodiment. The adsorbent 54 for removing blood cells is formed from a hydrophobic polymer resin. Consequently, the surface of the adsorbent 54 for removing blood cells is hydrophobic, and the resulting hydrophobic interactions are able to efficiently remove not only the granulocytes that function as inflammatory cells, but also the platelets. Moreover, inflammatory symptoms caused by autoimmune disease can be suppressed with minimal side-effects.

The same resins as those described above for the first embodiment may be used as the hydrophobic polymer resin. Accordingly, description of the resin is omitted here.

Ensuring that the surface Ra value of the adsorbent for removing blood cells is within a range from 5 to 100 nm enables a further improvement in the adsorption of white blood cells and platelets. As mentioned above, achieving a surface Ra value of less than 5 nm for the adsorbent for removing blood cells is problematic from a production perspective. In contrast, if the surface Ra value of the adsorbent for removing blood cells exceeds 100 nm, then the contribution of the adsorbent to the adsorption of platelets (size: 2 to 4 μm) tends to decrease. The surface Ra value of the adsorbent for removing blood cells can be measured using an AFM (atomic force microscope). In this embodiment, measurement of the surface Ra value of the adsorbent for removing blood cells is performed using an "SPA400" apparatus manufactured by Seiko Instruments, Inc. as the AFM and a "DFM SZDF20AL" (manufactured by Seiko Instruments, Inc.) as the probe, with the AFM measurement set to 10 μm×10 μm.

The adsorbent for removing blood cells formed from fibers according to the present embodiment is produced by a coagulation method comprising either the method of producing a hollow fiber-based adsorbent for removing blood cells described above or the method of producing a solid fiber-based adsorbent for removing blood cells described above.

Furthermore, the adsorbent for removing blood cells formed from fibers according to the present embodiment is composed of hollow fibers or solid fibers with an external diameter of 0.1 mm to 5 mm, and the average pore diameter on the surface of the adsorbent for removing blood cells formed from fibers of the present embodiment is within a range from 50 nm to 300 nm.

Because the fibers of the adsorbent for removing blood cells according to this embodiment are straight fibers, the adsorbent can be used more readily than adsorbents that employ an ultra-fine fibrous nonwoven fabric (such as the product "Cellsorba" manufactured by Asahi Kasei Corporation), even in those cases where the viscosity of the blood from the patient is high, and there is a high risk of problems such as coagulation within the blood cells removal module.

The mesh-like fabric used in the present embodiment is preferably composed of a mesh in which the fiber diameter (strand diameter) is within a range from 20 μm to 100 μm, and the number of strands of fiber per inch is within a range from 3 to 80 (3 to 80 mesh), and the material for the mesh may be selected from polyester, nylon, polyethylene and polypropylene.

Unlike LCAP (leukocytapheresis), the blood cells removal module according to this embodiment does not remove lymphocytes, meaning the danger of removing immunity-related memory cells is low. Further, as described below, the cylindrical adsorbent for removing blood cells that is used in the blood cells removal module according to this embodiment is capable of removing more platelets than an adsorbent "Adacolumn" (manufactured by JIMRO Co., Ltd.) formed from cellulose acetate beads that is used in GCAP (granulocytapheresis). As a result, inflammatory symptoms within a patient can be efficiently suppressed. Furthermore, with the blood cells removal module according to this embodiment, treatment can be performed simply by passing the whole blood through the module, and therefore the treatment is simple and safe, and does not require the expensive equipment such as a centrifuge that is used in conventional centrifuge methods.

EXAMPLES

Example 1

A polyarylate resin (hereafter abbreviated as "PAR", number average molecular weight: 25,000) was dissolved in NMP to prepare a polymer solution. The weight mixing ratio between the PAR and the NMP was set to 15.0:85.0. A mixture containing 60% of NMP in water was prepared as a coagulant. The polymer solution was added dropwise to the coagulant bath from a nozzle having an internal diameter of 0.25 mm and from a height approximately 10 cm above the liquid surface within the tank. Following thorough coagulation within the coagulant, the resulting beads were washed with distilled water, yielding beads for removing blood cells with a diameter of approximately 1.5 mm. These beads for removing blood cells of example 1 were substantially spherical, and the proportion (yield) of the beads having a shape that was usable as an adsorbent was 99.6% (calculated for 1,000 beads).

Figure 2:
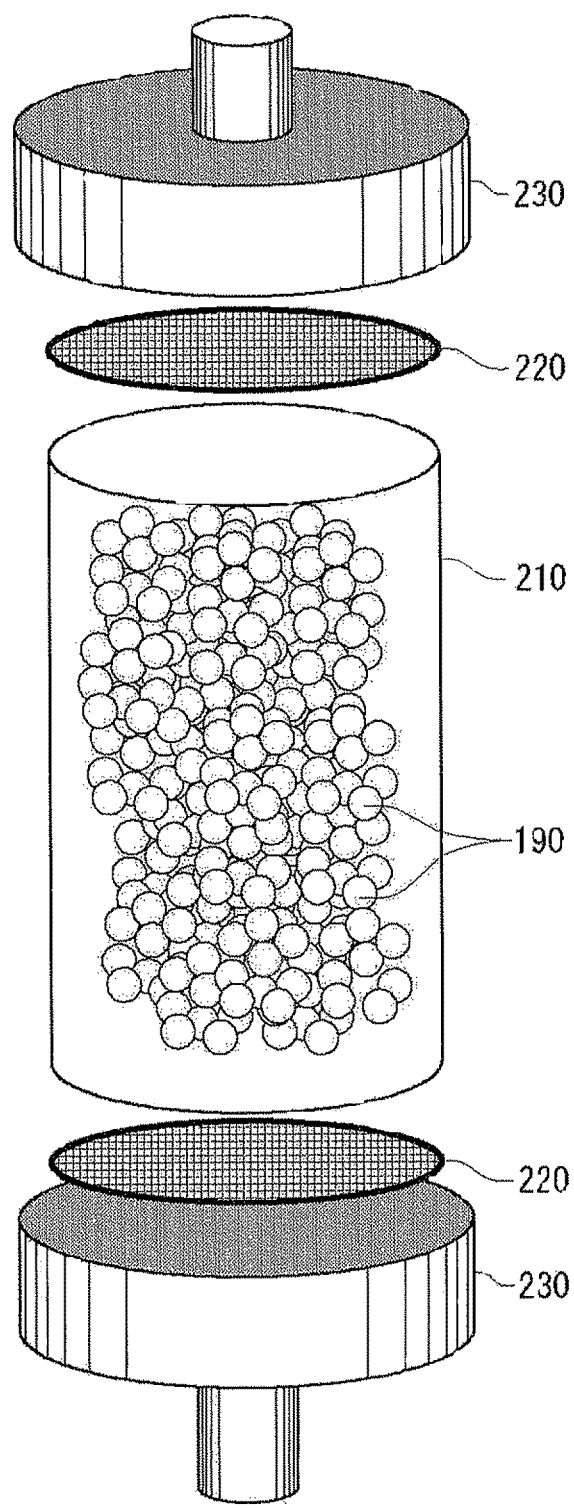
FIG. 2 is an exploded perspective view illustrating a general outline of a blood cells removal module using beads for removing blood cells according to example 1.

Subsequently, as illustrated in FIG. 2, the obtained beads 190 for removing blood cells were packed inside a circular cylindrical casing 210 produced from a polycarbonate, and with a pair of polyester meshes 220 positioned to prevent the beads 190 for removing blood cells from leaking out of the casing, headers 230 fitted with a blood inlet port and a blood outlet port respectively were attached to the casing to complete the module. The meshes 220 used had a mesh size that was finer than the diameter of the beads 190 for removing blood cells.

AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of example 1 was 15 nm.

Example 2

A polyethersulfone resin (hereafter abbreviated as "PES", grade: 4800P, number average molecular weight: 21,000) was dissolved in N-methyl-2-pyrrolidone (hereafter abbreviated as NMP) to prepare a polymer solution. The weight mixing ratio between the PES and the NMP was set to 15.0:85.0. A mixture containing 36% of NMP in water was prepared as a coagulant. The polymer solution was added dropwise to the coagulant bath from a nozzle having an internal diameter of 0.25 mm and from a height approximately 10 cm above the liquid surface within the tank. Following thorough coagulation within the coagulant, the resulting beads were washed with distilled water, yielding beads for removing blood cells with a diameter of approximately 1.5 mm. These beads for removing blood cells of example 2 were substantially spherical, and the proportion of the beads having a shape that was usable as an adsorbent was 99.8% (calculated for 1,000 beads). AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of example 2 was 21 nm.

Example 3

Figure 3:
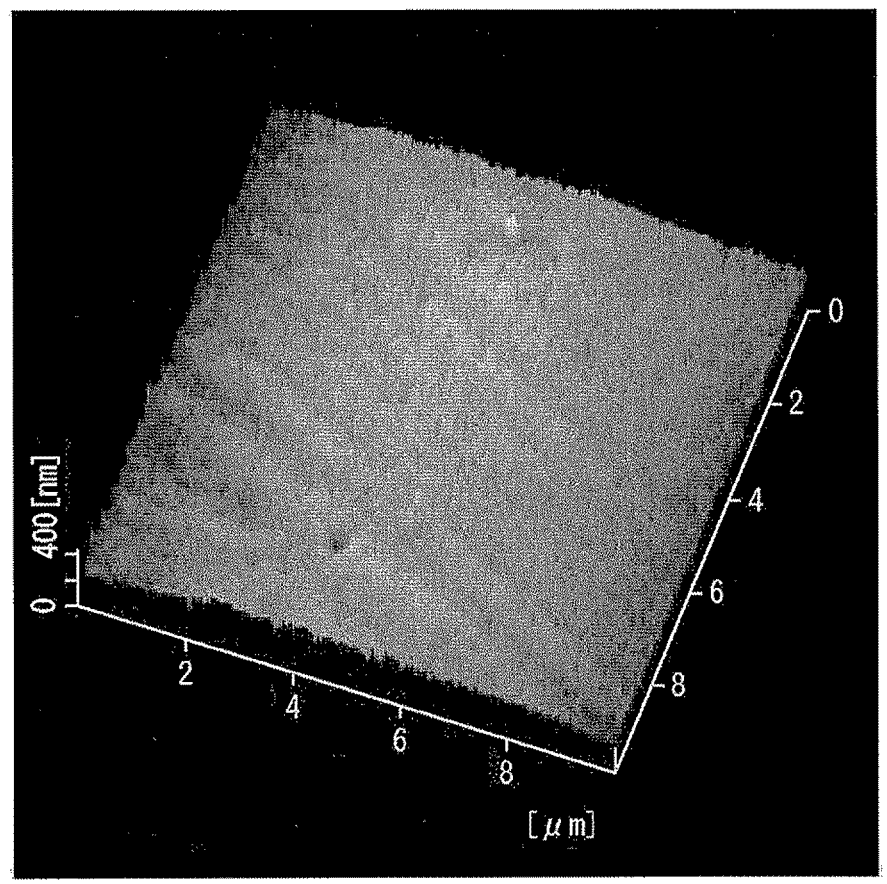
FIG. 3 is an AFM image (10 μm×10 μm) of beads for removing blood cells according to example 3.

APES (grade: 4800P, number average molecular weight: 21,000) and a PAR (number average molecular weight: 25,000) were dissolved in N-methyl-2-pyrrolidone (hereafter abbreviated as NMP) to prepare a polymer solution. The weight mixing ratio between the PES, the PAR and the NMP was set to 10.0:5.0:85.0. A mixture containing 36% of NMP in water was prepared as a coagulant. The polymer solution was added dropwise to the coagulant bath from a nozzle having an internal diameter of 0.25 mm and from a height approximately 10 cm above the liquid surface within the tank. Following thorough coagulation within the coagulant, the resulting beads were washed with distilled water, yielding beads for removing blood cells with a diameter of approximately 1.5 mm. These beads for removing blood cells of example 3 were substantially spherical, and the proportion of the beads having a shape that was usable as an adsorbent was 99.1% (calculated for 1,000 beads). AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of example 3 was 34 nm. An AFM image (10 μm×10 μm) of the beads for removing blood cells of example 3 is illustrated in FIG. 3.

Comparative Example 1

A polymer solution was prepared in the same manner as example 3. A mixture containing 70% of NMP in water was prepared as a coagulant. The polymer solution was added dropwise to the coagulant bath from a nozzle having an internal diameter of 0.25 mm and from a height approximately 10 cm above the liquid surface within the tank. Following thorough coagulation within the coagulant, the resulting beads were washed with distilled water, yielding beads for removing blood cells with a diameter of approximately 1.5 mm. These beads for removing blood cells of comparative example 1 were substantially spherical, and the proportion of the beads having a shape that was usable as an adsorbent was 72.3% (calculated for 1,000 beads). AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of comparative example 1 was 104 nm.

Comparative Example 2

Alumina balls with a diameter of 2 mm (manufactured by As One Corporation) were used as the beads for removing blood cells of comparative example 2. AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of comparative example 2 was 124 nm.

Comparative Example 3

Figure 4:
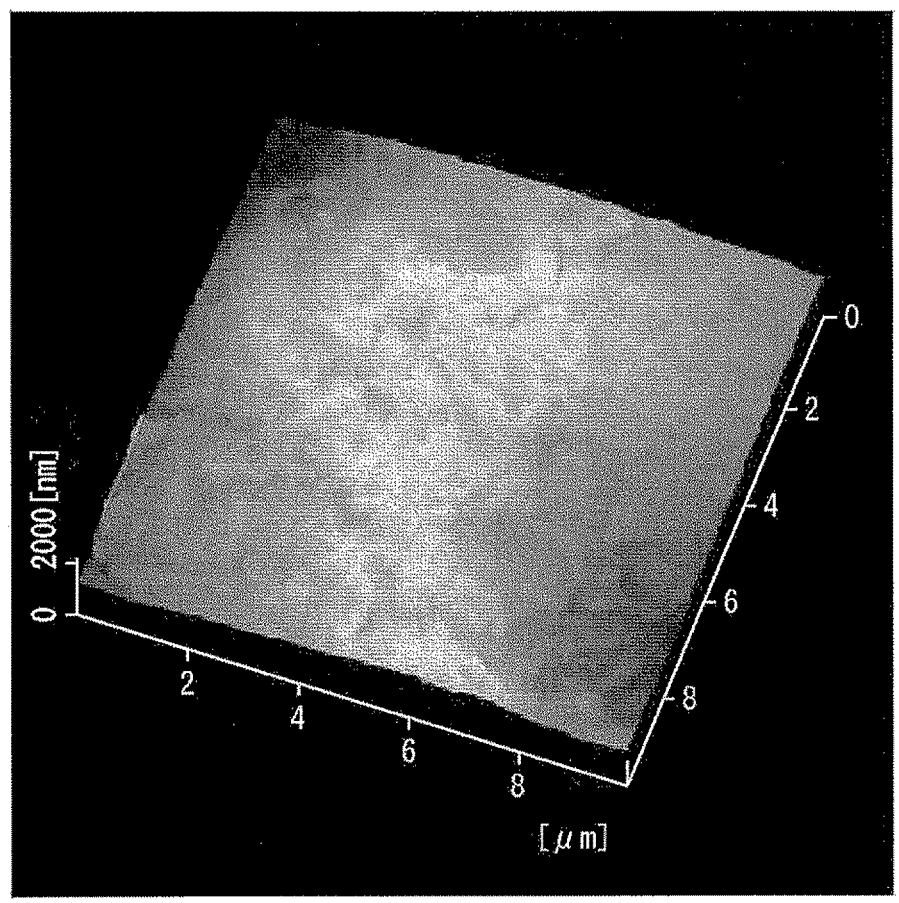
FIG. 4 is an AFM image (10 μm×10 μm) of beads for removing blood cells according to comparative example 3.

Cellulose acetate beads with a diameter of 2 mm (extracted from Adacolumn, manufactured by JIMRO Co., Ltd.) were used as the beads for removing blood cells of comparative example 3. AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads for removing blood cells of comparative example 3 was 133 nm. An AFM image (10 μm×10 μm) of the beads for removing blood cells of comparative example 3 is illustrated in FIG. 4. As is evident from FIG. 4, large surface irregularities exist on the surface of the beads for removing blood cells of comparative example 3.

[White Blood Cells—Platelets Adsorption Test]

A sample (38 mL) of each of the beads for removing blood cells from examples 1 to 3 and comparative examples 1 to 3 described above was used to fill a column of diameter 27 mm and length 70 min (internal volume: 40 mL). A 250 mL sample of blood from a healthy person was collected in a blood bag, and following heparinization, the blood was circulated through the column for 30 minutes at a rate of 7 mL/min, and the adsorption rates for the beads for removing blood cells were calculated from the changes in the number of granulocytes (neutrophils), the number of platelets and the number of lymphocytes. The results are listed in Table 1. Examples 2 and 3, and comparative examples 1 to 3 were converted to modules in the same manner as that described for example 1.

TABLE 1

|  | Adsorbent | Ra (nm) | Yield | Granulocyte adsorption (%) | Lymphocyte adsorption (%) | Platelet adsorption (%) | Coagulation during and after circulation |
|---|---|---|---|---|---|---|---|
| Example 1 | Polyarylate beads | 15 | 99.6 | 62 | 5 | 59 | No coagulation or blood retention |
| Example 2 | Polyethersulfone beads | 21 | 99.8 | 55 | 2 | 48 | No coagulation or blood retention |
| Example 3 | Polyarylate-Polyethersulfone beads | 34 | 99.1 | 57 | 4 | 57 | No coagulation or blood retention |
| Comparative example 1 | Polyarylate-Polyethersulfone beads | 104 | 72.3 | 65 | 6 | 62 | No coagulation or blood retention |

TABLE 1-continued

| Adsorbent | | Ra (nm) | Yield | Granulocyte adsorption (%) | Lymphocyte adsorption (%) | Platelet adsorption (%) | Coagulation during and after circulation |
|---|---|---|---|---|---|---|---|
| Comparative example 2 | Alumina balls | 124 | — | 62 | 10 | 61 | Coagulation during circulation |
| Comparative example 3 | Cellulose acetate beads | 133 | — | 51 | 0 | 19 | No coagulation or blood retention |

For the beads for removing blood cells of comparative example 1 (Ra=104 nm), the yield of beads having a shape that was usable as an adsorbent decreased significantly, which causes an increase in the production costs. For the beads for removing blood cells of comparative example 2 (Ra=124 nm), although adsorption of white blood cells and platelets was confirmed, a problem occurred in that the blood coagulated during circulation through the column. For the beads for removing blood cells of comparative example 3 (Ra=133 nm), the adsorption of platelets was found to be poor.

For the beads for removing blood cells according to examples 1 to 3, it was found that white blood cells and platelets were able to be adsorbed efficiently, with no coagulation or retention of the blood, either during or after circulation through the column.

Example 4

Figure 5:
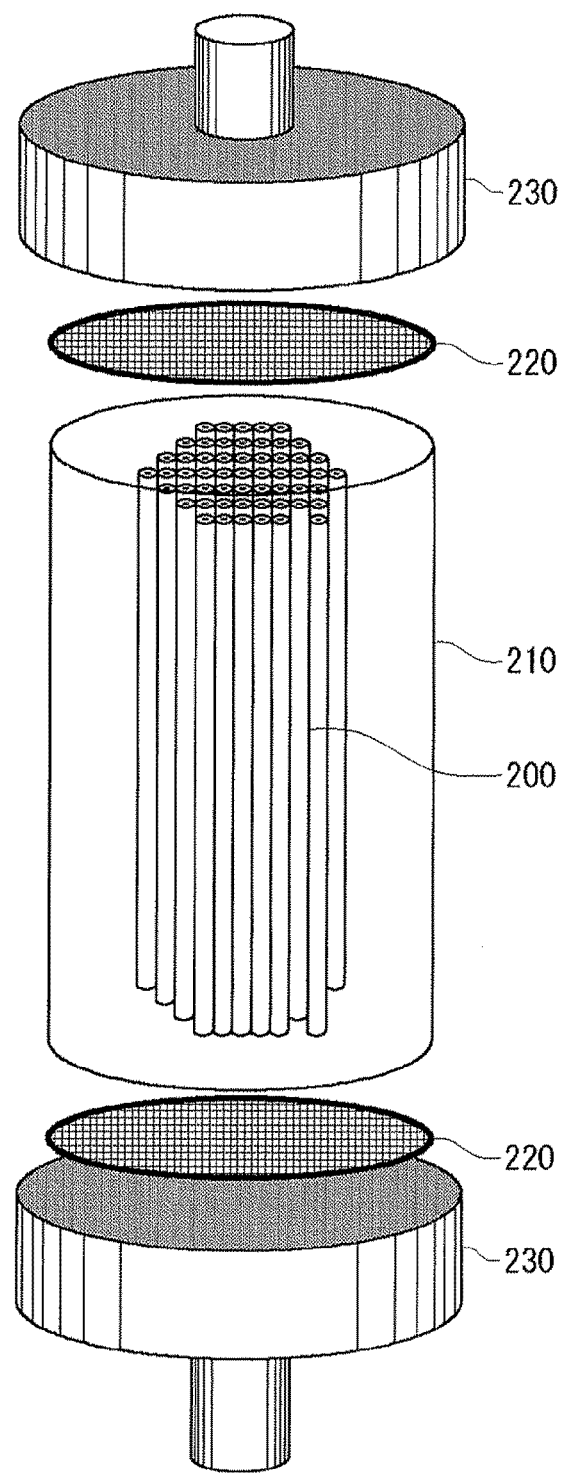
FIG. 5 is an exploded perspective view illustrating a general outline of a blood cells removal module using hollow fibers according to example 4.

A polymer solution was prepared using a PAR, a PES and NMP. The mixing weight ratio between the PAR and the PES was 1:1. An NMP aqueous solution was used as a coagulant and a core liquid. Using a double spinneret, the polymer solution was discharged, together with the core liquid, into the above coagulant to prepare hollow fibers for removing blood cells, and 10,000 of these hollow fibers for removing blood cells were bundled together to form a hollow fiber bundle. As illustrated in FIG. 5, this hollow fiber bundle 200 was packed inside a cylindrical casing 210 produced from a polycarbonate, and with a pair of polyester meshes 220 pressed against the hollow fiber bundle, headers 230 fitted with a blood inlet port and a blood outlet port respectively were attached to the casing to complete the module. The meshes 220 used had a mesh size that was finer than the diameter of the hollow fibers. AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the hollow fibers for removing blood cells of example 4 was 5.2 nm.

Comparative Example 4

For comparative example 4, the filler from the granulocyte adsorption column Adacolumn (cellulose acetate beads with a diameter of approximately 2 mm) was used. AFM measurements (10 μm×10 μm, SPA400 apparatus manufactured by Seiko Instruments, Inc., probe: DFM SZDF20AL manufactured by Seiko Instruments, Inc.) confirmed that the surface Ra value for the beads of comparative example 4 was 133 nm.

[White Blood Cells—Platelets Adsorption Test]

Samples equivalent to a surface area of 3,260 cm² of the hollow fibers for removing blood cells of example 4 and the beads of comparative example 4 were each used to fill a column of diameter 27 mm and length 70 mm (internal volume: 40 mL). A 250 mL sample of blood from a healthy person was collected in a blood bag, and following heparinization, the blood was circulated through the column for 30 minutes at a rate of 7 mL/min, and the adsorption rates for the module were calculated from the changes in the number of granulocytes (neutrophils), the number of platelets and the number of lymphocytes. The results are listed in Table 2.

TABLE 2

| | Adsorption rate (n = 6) | | |
|---|---|---|---|
| | Granulocytes (neutrophils) | Platelets | Lymphocytes |
| Example 4 | 67% | 78% | 0% |
| Comparative example 4 | 57% | 19% | 0% |

As is evident from Table 2, when the hollow fibers for removing blood cells of example 4 were used, it was confirmed that both the granulocytes and platelets were removed efficiently. In contrast, when the beads of comparative example 4 were used, the removal of the platelets was inadequate.

Example 5

A polymer stock solution was prepared using a polyarylate resin (hereafter abbreviated as "PAR", number average molecular weight: 25,000, product name: U polymer, manufactured by Unitika Ltd.), a polyethersulfone resin (hereafter abbreviated as "PES", grade: 4800P, number average molecular weight: 21,000, product name: Sumikaexcel PES, manufactured by Sumitomo Chemical Co., Ltd.) and N-methylpyrrolidone (NMP). The weight mixing ratio between the PAR, the PES and the NMP was set to 7.5:7.5:85.0. An aqueous solution of N-methylpyrrolidone (a mixture containing 60% of NMP in water) was used as a coagulant and a core liquid. Using a double spinneret, the above polymer stock solution was discharged, together with the core liquid, into the coagulant to prepare a hollow fiber membrane, and this membrane was cut in a continuous manner, yielding an adsorbent for removing blood cells composed of short hollow fibers with an external diameter of 0.3 mm, an internal diameter of 0.2 mm and a length of 5 mm. Although there are no particular limitations on the technique employed for cutting the hollow fiber membrane into short fibers, from an industrial viewpoint, a conventional cutting apparatus using a cutter roller (for example, see JP 05-96033 U, JP 09-277190 A and JP 06-27092 U) is ideal.

Measurement of the surface roughness of the adsorbent for removing blood cells according to this example using an AFM (10 μm×10 μm, SPA400 apparatus manufactured by Seiko Instruments, Inc., probe: DFM SZDF20AL manufactured by Seiko Instruments, Inc.) yielded a result of Ra=6.2 nm. Further, the average pore diameter was 25.4 nm. The average pore diameter was measured using a porosimeter (PoreMaster-60) manufactured by Yuasa Ionics Inc.

A white blood cells and platelets adsorption test was performed by packing a quantity of the short fibers equivalent to a total external surface area of approximately 0.1 m² into a polycarbonate casing (column) with an internal diameter of 27 mm and a length of 70 mm. The ratio of the length of the adsorbent for removing blood cells relative to the internal diameter of the casing was 5 mm/27 mm×100=18.5%. The filling rate of the adsorbent for removing blood cells relative to the volume of the casing was 48%.

A 250 mL sample of blood from a healthy person was collected in a blood bag, and following heparinization, the blood was circulated through the column for 30 minutes at a rate of 7 mL/min, and the adsorption rates for the adsorbent for removing blood cells according to example 5 were calculated from the changes in the number of granulocytes (neutrophils), the number of platelets and the number of lymphocytes. The results revealed adsorption rates for the granulocytes, platelets and lymphocytes of 54%, 61% and 2% respectively.

The adsorbent for removing blood cells according to example 5 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 6

A hollow fiber membrane was prepared using the same method as that described for example 5, and the resulting hollow fiber membrane was cut to lengths of 10 mm (external diameter: 0.3 mm, internal diameter: 0.2 mm), yielding an adsorbent for removing blood cells composed of short hollow fibers. The ratio of the length of the adsorbent for removing blood cells relative to the internal diameter of the casing was 10 mm/27 mm×100=37.0%. The filling rate of the adsorbent for removing blood cells relative to the volume of the casing was 36%.

The adsorbent for removing blood cells according to example 6 was subjected to the same blood cells adsorption test as that described above for example 5. The test results revealed adsorption rates for the granulocytes, platelets and lymphocytes of 55%, 58% and 3% respectively.

The adsorbent for removing blood cells according to example 6 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 7

A hollow fiber membrane was prepared using the same method as that described for example 5, and the resulting hollow fiber membrane was cut to lengths of 15 mm (external diameter: 0.3 mm, internal diameter: 0.2 mm), yielding an adsorbent for removing blood cells composed of short hollow fibers. The ratio of the length of the adsorbent for removing blood cells relative to the internal diameter of the casing was 15 mm/27 mm×100=55.6%. The filling rate of the adsorbent for removing blood cells relative to the volume of the casing was 21%.

The adsorbent for removing blood cells according to example 7 was subjected to the same blood cells adsorption test as that described above for example 5. The test results revealed adsorption rates for the granulocytes, platelets and lymphocytes of 51%, 55% and 3% respectively.

The adsorbent for removing blood cells according to example 7 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Comparative Example 5

A hollow fiber membrane was prepared using the same method as that described for example 5, and the resulting hollow fiber membrane was cut to lengths of 20 mm (external diameter: 0.3 mm, internal diameter: 0.2 mm), yielding an adsorbent for removing blood cells composed of short hollow fibers. The ratio of the length of the adsorbent for removing blood cells relative to the internal diameter of the casing was 20 mm/27 mm×100=74.1%. The filling rate of the adsorbent for removing blood cells relative to the volume of the casing was 15%.

The adsorbent for removing blood cells according to comparative example 5 was subjected to the same blood cells adsorption test as that described above for example 5. The test results revealed adsorption rates for the granulocytes, platelets and lymphocytes of 53%, 57% and 2% respectively.

The adsorbent for removing blood cells according to comparative example 5 exhibited a satisfactory adsorption capacity for the granulocytes and platelets that function as inflammatory cells, but a low adsorption capacity for the lymphocytes, which function as memory cells and are preferably retained within the body. However, because movement of the fibers inside the casing was restricted, air bubbles tended to be trapped by the fibers, making air removal during priming difficult, and by the completion of the blood circulation process, blood coagulation was visible on the adsorbent for removing blood cells.

Example 8

A polymer stock solution was prepared using a PAR (number average molecular weight: 25,000, product name: U polymer, manufactured by Unitika Ltd.) and NMP. The weight mixing ratio between the PAR and the NMP was set to 15:85. An aqueous solution of N-methylpyrrolidone (a mixture containing 60% of NMP in water) was used as a coagulant. Using a spinneret, the above polymer stock solution was discharged into the coagulant to prepare a solid fiber, and this film was cut in a continuous manner, yielding an adsorbent for removing blood cells composed of short solid fibers with an external diameter of 0.25 mm and a length of 5 mm. The ratio of the length of the adsorbent for removing blood cells relative to the internal diameter of the casing was 5 mm/27 mm×100=18.5%. The filling rate of the adsorbent for removing blood cells relative to the volume of the casing was 42%.

Measurement of the surface roughness of the adsorbent for removing blood cells according to this example using an AFM (10 μm×10 μm, SPA400 apparatus manufactured by Seiko Instruments, Inc., probe: DFM SZDF20AL manufactured by Seiko Instruments, Inc.) yielded a result of Ra=3.4 nm. Further, the average pore diameter was 16.7 nm. The average pore diameter was measured using a porosimeter (PoreMaster-60) manufactured by Yuasa Ionics Inc.

The adsorbent for removing blood cells according to example 8 was subjected to the same blood cells adsorption test as that described above for example 5. The test results revealed adsorption rates for the granulocytes, platelets and lymphocytes of 65%, 62% and 6% respectively.

The adsorbent for removing blood cells according to example 8 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 9

A solid fiber was prepared using the same method as that described for example 8, and the resulting solid fiber was cut to lengths of 10 mm (external diameter: 0.25 mm), yielding an adsorbent for removing blood cells composed of short solid fibers. The ratio of the length of the adsorbent for removing blood cells relative to the internal diameter of the casing was 10 mm/27 mm×100=37.0%. The filling rate of the adsorbent for removing blood cells relative to the volume of the casing was 31%.

The adsorbent for removing blood cells according to example 9 was subjected to the same blood cells adsorption test as that described above for example 5. The test results revealed adsorption rates for the granulocytes, platelets and lymphocytes of 66%, 60% and 7% respectively.

The adsorbent for removing blood cells according to example 9 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 10

A solid fiber was prepared using the same method as that described for example 8, and the resulting solid fiber was cut to lengths of 15 mm (external diameter: 0.25 mm), yielding an adsorbent for removing blood cells composed of short solid fibers. The ratio of the length of the adsorbent for removing blood cells relative to the internal diameter of the casing was 15 mm/27 mm×100=55.6%. The filling rate of the adsorbent for removing blood cells relative to the volume of the casing was 20%.

The adsorbent for removing blood cells according to example 10 was subjected to the same blood cells adsorption test as that described above for example 5. The test results revealed adsorption rates for the granulocytes, platelets and lymphocytes of 64%, 58% and 5% respectively.

The adsorbent for removing blood cells according to example 10 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 11

A polymer stock solution was prepared using a PES (grade: 4800P, number average molecular weight: 21,000, product name: Sumikaexcel PES, manufactured by Sumitomo Chemical Co., Ltd.) and NMP. The weight mixing ratio between the PES and the NMP was set to 15:85. An aqueous solution of N-methylpyrrolidone (a mixture containing 60% of NMP in water) was used as a coagulant. Using a spinneret, the above polymer stock solution was discharged into the coagulant to prepare a solid fiber, and this film was cut in a continuous manner, yielding an adsorbent for removing blood cells composed of short solid fibers with an external diameter of 0.25 mm and a length of 10 mm. The ratio of the length of the adsorbent for removing blood cells relative to the internal diameter of the casing was 10 mm/27 mm×100=37%. The filling rate of the adsorbent for removing blood cells relative to the volume of the casing was 28%.

Measurement of the surface roughness of the adsorbent for removing blood cells according to this example using an AFM (10 μm×10 μm, SPA400 apparatus manufactured by Seiko Instruments, Inc., probe: DFM SZDF20AL manufactured by Seiko Instruments, Inc.) yielded a result of Ra=5.2 nm. Further, the average pore diameter was 12.4 nm. The average pore diameter was measured using a porosimeter (PoreMaster-60) manufactured by Yuasa Ionics Inc.

The adsorbent for removing blood cells according to example 11 was subjected to the same blood cells adsorption test as that described above for example 5. The test results revealed adsorption rates for the granulocytes, platelets and lymphocytes of 53%, 48% and 0% respectively.

The adsorbent for removing blood cells according to example 11 exhibited a satisfactory adsorption capacity for the granulocytes and platelets that function as inflammatory cells, but a low adsorption capacity for the lymphocytes, which function as memory cells and are preferably retained within the body. Furthermore, air removal during priming was simple, and no coagulation of the blood was observed.

Example 12

A hollow fiber membrane (internal diameter: 200 μm, external diameter: 230 μm) was extracted from a dialyzer FB-150F manufactured by Nipro Corporation that used the cellulose acetate hollow fiber membrane, and the film was cut into 10 mm lengths, yielding an adsorbent for removing blood cells composed of short hollow fibers. The filling rate of the adsorbent for removing blood cells relative to the volume of the casing was 31%.

The adsorbent for removing blood cells according to example 12 was subjected to the same blood cells adsorption test as that described above for example 5. The test results revealed adsorption rates for the granulocytes, platelets and lymphocytes of 55%, 15% and 1% respectively.

The adsorbent for removing blood cells according to example 12 exhibited a satisfactory adsorption capacity for the granulocytes that function as inflammatory cells. In contrast, the adsorption capacity for the platelets and lymphocytes was low. Air removal during priming was simple, and no coagulation of the blood was observed.

Table 3 below summarizes various information and the results of the blood cells adsorption tests for the adsorbents for removing blood cells of examples 5 to 12 and comparative example 5.

TABLE 3

| Absorbent for removing blood cells | Fiber length (mm) | Ratio with internal diameter of casing (%) | Granulocyte absorption (%) | Lymphocyte absorption (%) | Platelet absorption (%) | State of air removal and blood coagulation | Filling rate of absorbent for removing blood cells (%) |
|---|---|---|---|---|---|---|---|
| Example 5 | Polyarylate Polyethersulfone hollow fibers | 5 | 18.5 | 54 | 2 | 61 | Good air removal, no blood coagulation | 48 |
| Example 6 | Polyarylate Polyethersulfone hollow fibers | 10 | 37.0 | 55 | 3 | 58 | Good air removal, no blood coagulation | 36 |
| Example 7 | Polyarylate Polyethersulfone hollow fibers | 15 | 55.6 | 51 | 3 | 55 | Good air removal, no blood coagulation | 21 |
| Comparative example 5 | Polyarylate Polyethersulfone hollow fibers | 20 | 74.1 | 53 | 2 | 57 | Good air removal, some blood coagulation | 15 |
| Example 8 | Polyarylate solid fibers | 5 | 18.5 | 65 | 6 | 62 | Good air removal, no blood coagulation | 42 |
| Example 9 | Polyarylate solid fibers | 10 | 37.0 | 66 | 7 | 60 | Good air removal, no blood coagulation | 31 |
| Example 10 | Polyarylate solid fibers | 15 | 55.6 | 64 | 5 | 58 | Good air removal, no blood coagulation | 20 |
| Example 11 | Polyethersulfone solid fibers | 10 | 37.0 | 53 | 0 | 48 | Good air removal, no blood coagulation | 28 |
| Example 12 | Cellulose triacetate hollow fibers | 10 | 37.0 | 55 | 1 | 15 | Good air removal, no blood coagulation | 31 |

Example 13

A polymer stock solution was prepared using a polyarylate resin (hereafter abbreviated as "PAR", number average molecular weight: 25,000, product name: U polymer, manufactured by Unitika Ltd.), a polyethersulfone resin (hereafter abbreviated as "PES", grade: 4800P, number average molecular weight: 21,000, product name: Sumikaexcel PES, manufactured by Sumitomo Chemical Co., Ltd.) and N-methylpyrrolidone (NMP). The weight mixing ratio between the PAR, the PES and the NMP was set to 7.5:7.5:85.0. An aqueous solution of N-methylpyrrolidone (a mixture containing 60% of NMP in water) was used as a coagulant and a core liquid. Using a double spinneret, the above polymer stock solution was discharged, together with the core liquid, into the coagulant to prepare a hollow fiber membrane, and this film was cut in a continuous manner, yielding an adsorbent for removing blood cells composed of short hollow fibers with an external diameter of 300 μm, an internal diameter of 200 μm and a length of 70 mm.

Measurement of the surface roughness of the adsorbent for removing blood cells according to this example using an AFM (10 μm×10 μm, SPA400 apparatus manufactured by Seiko Instruments, Inc., probe: DFM SZDF20AL manufactured by Seiko Instruments, Inc.) yielded a result of Ra=5.2 nm. Further, the average pore diameter was 25.4 nm.

Approximately 3,500 strands of the hollow fibers of the adsorbent for removing blood cells according to this example (external diameter: 300 μm, length 70 mm) were aligned on a flat surface, a polyester resin mesh (70 mesh, thread diameter: 71 μm) that functioned as a mesh-like fabric was overlaid on top of the hollow fibers, and a heat sealer was then used to fuse both ends of the adsorbent for removing blood cells to the mesh, thereby sealing the end faces of the adsorbent for removing blood cells (total adsorption surface area: approximately 2,300 cm$^2$). Subsequently, the end portions on the outside of the fused portions were cut off and discarded, and the mesh-like fabric was rolled along the direction of alignment of the adsorbent for removing blood cells, thus forming a cylindrical adsorbent for removing blood cells composed of a bundle of the fibers of the adsorbent for removing blood cells with the mesh-like fabric interposed therebetween as a spacer.

As illustrated in FIG. 8, the obtained cylindrical adsorbent 350 for removing blood cells was packed inside a casing 20 produced from a polycarbonate (total length: 70 mm, internal diameter: 27 mm, volume: 40 mL), and a pair of headers 40a and 40b fitted with a blood inlet and a blood outlet respectively were attached to the casing to complete preparation of a blood cells removal module A.

Comparative Example 6

The filler from the granulocyte adsorption column Adacolumn (manufactured by JIMRO Co., Ltd.) (cellulose acetate beads with a diameter of approximately 2 mm, Ra=133 nm) was packed inside a polycarbonate casing of the same type as that used in example 13 (total length: 70 mm, internal diameter: 27 mm, volume: 40 mL), and a pair of headers fitted with a blood inlet and a blood outlet respectively were attached to the casing to complete preparation of a blood cells removal module B.

[Method of Evaluation]

A 500 mL sample of blood was collected from a healthy person, and following heparinization, the blood was divided into two blood bags of 250 mL, one sample was circulated through each of the two modules for 30 minutes at a rate of 7 mL/min, and the adsorption rates for each blood cells removal module were calculated from the changes in the number of granulocytes (neutrophils), the number of platelets and the number of lymphocytes. The results are listed below in Table 4. These results represent the average values for the results of 6 separate measurements.

TABLE 4

| | Adsorption rate (%) | | |
|---|---|---|---|
| | Granulocytes (neutrophils) | Platelets | Lymphocytes |
| Example 13 | 67 | 78 | 0 |
| Comparative example 6 | 57 | 19 | 0 |

From the results in Table 4 it is evident that the blood cells removal module A of example 13 exhibited a platelet adsorption rate that was far superior to that of the blood cells removal module B of comparative example 6.

Example 14

Approximately 8,000 strands of the hollow fibers of the adsorbent for removing blood cells obtained in example 13 (external diameter: 300 µm, length 70 mm) were aligned on a flat surface, a polyester resin mesh (70 mesh, thread diameter: 100 µm) that functioned as a mesh-like fabric was overlaid on top of the hollow fibers, and a heat sealer was then used to fuse both ends of the adsorbent for removing blood cells to the mesh, thereby sealing the end faces of the adsorbent for removing blood cells (total adsorption surface area: approximately 0.9 m$^2$). Subsequently, the end portions on the outside of the fused portions were cut off and discarded, and the mesh-like fabric was rolled along the direction of alignment of the adsorbent for removing blood cells, thus forming a cylindrical adsorbent for removing blood cells composed of a bundle of the fibers of the adsorbent for removing blood cells with the mesh-like fabric interposed therebetween as a spacer.

As illustrated in FIG. 8, the obtained cylindrical adsorbent 350 for removing blood cells was packed inside a polycarbonate casing 20 (total length: 185 mm, internal diameter: 59 mm, volume: 324 mL), and a pair of headers 40a and 40b fitted with a blood inlet and a blood outlet respectively were attached to the casing to complete preparation of a blood cells removal module C.

REFERENCE EXAMPLE

A polymer stock solution was prepared using a polyarylate resin (hereafter abbreviated as "PAR", number average molecular weight: 25,000, product name: U polymer, manufactured by Unitika Ltd.), a polyethersulfone resin (hereafter abbreviated as "PES", grade: 4800P, number average molecular weight: 21,000, product name: Sumikaexcel PES, manufactured by Sumitomo Chemical Co, Ltd.) and N-methylpyrrolidone (NMP). The weight mixing ratio between the PAR, the PES and the NMP was set to 7.5:7.5:85.0. An aqueous solution of N-methylpyrrolidone (a mixture containing 60% of NMP in water) was used as a coagulant. The polymer solution was added dropwise to the coagulant bath from a nozzle having an internal diameter of 0.25 mm and from a height approximately 20 cm above the liquid surface within the tank. Following thorough coagulation within the coagulant, the resulting beads were washed with distilled water, yielding beads for removing blood cells with a diameter of approximately 1 mm.

Approximately 300,000 of the beads for removing blood cells obtained in this reference example (approximately 290 mL) (adsorption surface area: approximately 0.9 m$^2$) were packed in a polycarbonate casing (total length: 185 mm, internal diameter: 59 mm, volume: 324 mL), and a pair of headers 40a and 40b fitted with a blood inlet and a blood outlet respectively were attached to the casing to complete preparation of a blood cells removal module D.

[Method of Evaluation]

3 L of heparinized bovine blood (hematocrit value: 32%) was circulated through each of the blood cells removal modules at a rate of 50 mL/min, and after 20 minutes, the inlet pressure at the blood inlet of the blood cells removal module and the outlet pressure at the blood outlet were measured, and the pressure loss within the module was calculated. The results are listed below in Table 5.

TABLE 5

| | Module inlet pressure (Pa) | Module outlet pressure (Pa) | Pressure loss (Pa) |
|---|---|---|---|
| Reference Example | 6,000 | 3,866 | 2,133 |
| Example 14 | 4,666 | 4,000 | 666 |

From the results in Table 5 it is evident that the blood cells removal module C of example 14 had a smaller pressure loss than that of the blood cells removal module D that was filled with the beads of the reference example. The granulocyte (neutrophil) and platelet adsorption rates for the blood cells removal module C of example 14 were substantially the same as those for the blood cells removal module D filled with the beads of the reference example.

[Addendum]

Another preferred embodiment of the present invention is described below.

A blood cells removal module according to an embodiment of the present invention comprises a casing provided with an inlet for introducing a blood flow prior to blood cells removal and an outlet for discharging the blood flow following blood cells removal, an adsorbent for removing blood cells composed of short fibers that is housed inside the casing, and meshes that are provided on the inside of the inlet and outlet respectively and retain the adsorbent for removing blood cells within the casing, wherein the length of the adsorbent for removing blood cells is within a range from 1 to 60% of the internal diameter of the casing.

According to this embodiment, white blood cells and platelets can be removed efficiently while problems such as air removal prior to use and in-circuit coagulation during blood flow are suppressed. The length of the adsorbent for removing blood cells is preferably within a range from 18 to 56% of the internal diameter of the casing. This enables the above effects to be further enhanced.

In the above embodiment, the filling rate of the adsorbent for removing blood cells relative to the volume of the casing may be within a range from 20 to 60%.

Further, in the above embodiment, the adsorbent for removing blood cells may be composed of hollow fibers or solid fibers. In those cases where the adsorbent for removing blood cells is composed of hollow fibers, the amount of material used can be reduced compared with those cases where solid fibers are used. Furthermore, hollow fibers also offer the advantage that blood cell adsorption on the internal surfaces of the fibers can also be expected.

Furthermore, in the above embodiment, the adsorbent for removing blood cells may be formed from a hydrophobic polymer resin. In this case, the hydrophobic polymer resin may be a polyarylate resin having a repeating unit represented by chemical formula (1) shown below.

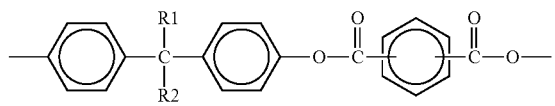

(1)

Furthermore, the hydrophobic polymer resin may comprise a polyethersulfone resin having a repeating unit represented by chemical formula (2) or chemical formula (3) shown below.

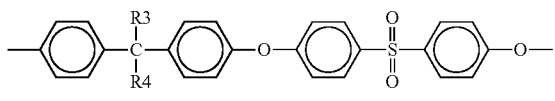

(2)

In chemical formula (2), each of R3 and R4 represents a lower alkyl group of 1 to 5 carbon atoms, and R3 and R4 may be the same or different.

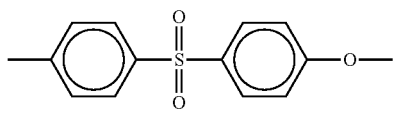

(3)

In the above embodiment, the hydrophobic polymer resin may include a polyarylate resin having a repeating unit represented by chemical formula (1) shown above, and a polyethersulfone resin having a repeating unit represented by chemical formula (2) or chemical formula (3) shown above.

The blood cells removal module of the above embodiment may be used for removing white blood cells and platelets from blood.

Moreover, appropriate combinations of each of the elements described above are also deemed to be included within the scope of the invention for which patent protection is sought on the basis of the present description.

Furthermore, other preferred embodiments of the present invention are described below.

(I) A blood cells removal module comprising a casing provided with an inlet for introducing a blood flow prior to blood cells removal and an outlet for discharging the blood flow following blood cells removal, and a cylindrical adsorbent for removing blood cells, which is formed by rolling an integrated blood cells removal adsorbent-containing mesh-like fabric, in which an adsorbent for removing blood cells that is formed from a plurality of aligned hollow fibers or solid fibers is secured at both ends to a mesh-like fabric that is permeable to blood, along the direction of alignment of the adsorbent for removing blood cells.

(II) The blood cells removal module according to (I) above, further comprising meshes which are provided on the inside of the inlet and outlet respectively, and retain the adsorbent for removing blood cells within the casing.

(III) The blood cells removal module according to (I) or (II) above, wherein the adsorbent for removing blood cells comprises at least hydrophobic polymer resin selected from amongst polyarylate resins having a repeating unit represented by chemical formula (1) shown below, and polyethersulfone resins having a repeating unit represented by chemical formula (2) or chemical formula (3) shown below.

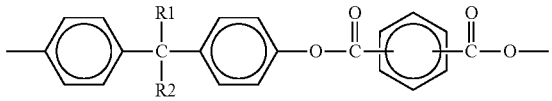

(1)

In chemical formula (1), each of R1 and R2 represents a lower alkyl group of 1 to 5 carbon atoms, and R1 and R2 may be the same or different.

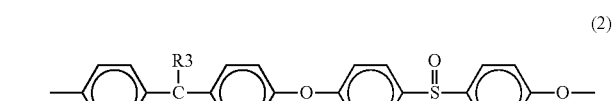

(2)

In chemical formula (2), each of R3 and R4 represents a lower alkyl group of 1 to 5 carbon atoms, and R3 and R4 may be the same or different.

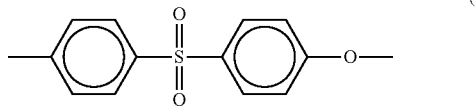

(3)

(IV) The blood cells removal module according to any one of (I) to (III) above, which is used for removing white blood cells and platelets from blood.

(V) A method of producing a blood cells removal module, the method comprising: forming an integrated blood cells removal adsorbent-containing mesh-like fabric by securing both ends of an adsorbent for removing blood cells that is formed from a plurality of aligned hollow fibers or solid fibers to a mesh-like fabric that is permeable to blood, forming a cylindrical adsorbent for removing blood cells by rolling the integrated blood cells removal adsorbent-containing mesh-like fabric along the direction of alignment of the adsorbent for removing blood cells, and housing the cylindrical adsorbent for removing blood cells inside a casing provided with an inlet for introducing a blood flow prior to blood cells removal and an outlet for discharging the blood flow following blood cells removal.

(VI) The method of producing a blood cells removal module according to (V) above, wherein when forming the integrated blood cells removal adsorbent-containing mesh-like fabric, the adsorbent for removing blood cells is composed of hollow fibers, and in those cases where both ends of the adsorbent for removing blood cells are secured by thermal fusion to the mesh-like fabric that is permeable to blood, the hollows are sealed at both ends of the thermally fused adsorbent for removing blood cells.

According to the embodiment described above, the pressure loss during blood cells removal can be reduced compared with the case of an adsorbent for removing blood cells composed of beads.

Further, the mesh-like fabric functions as a spacer for the adsorbent for removing blood cells formed from the plurality of hollow fibers or solid fibers, meaning the distance between individual fibers of the adsorbent for removing blood cells is substantially uniform throughout the blood cells removal module and is formed with an appropriate spacing. Accordingly, stagnation of the blood flow through the blood cells removal module is suppressed. As a result, the blood cells adsorption efficiency improves, and because unlike conventional adsorbents, the ends of the adsorbent for removing blood cells composed of fibers need not necessarily be secured using a mesh, the number of components can be reduced and the production process can be simplified.

Furthermore, in those cases where the adsorbent for removing blood cells is composed of hollow fibers, because the hollows at both end faces of the thermally fused adsorbent for removing blood cells are sealed, penetration of the blood into the interior of the hollow fibers of the adsorbent for removing blood cells during blood cells removal can be suppressed, thereby preventing blood retention.

Although the present invention has been described above in detail, the scope of the present invention is not limited by the preceding description.

Furthermore, the detailed description of the invention, the claims, the drawings and the abstract of each of the specifications disclosed in Japanese Patent Application No. 2008-109381 filed on Apr. 18, 2008, Japanese Patent Application No. 2008-154418 filed on Jun. 12, 2008, Japanese Patent Application No. 2008-299521 filed on Nov. 25, 2008, and Japanese Patent Application No. 2009-098289 filed on Apr. 14, 2009 are incorporated within this application.

INDUSTRIAL APPLICABILITY

The present invention is ideal for applications for the removal of blood cells.

Reference Numerals 1, 10, 300: Blood cells removal module
20: Casing
21: Casing main body
22, 24: Blood flow inlet and outlet
30a, 30b: Mesh
40a, 40b: Header
350, 350a: Cylindrical adsorbent for removing blood cells
52: Mesh-like fabric
54: Adsorbent for removing blood cells
56: Fused portion
60: Integrated blood cells removal adsorbent-containing mesh-like fabric
70: Fusion device
100: Blood cells removal beads production apparatus
110: Stock solution tank
120: Pump
130: Nozzle
140: Coagulant bath
144: Coagulant collection tank
150: Beads for removing blood cells

The invention claimed is:

1. An adsorbent for removing blood cells, used for removing white blood cells and platelets from blood, which is formed from a hydrophobic polymer resin, and has a surface center line average roughness of 5 to 100 nm, and
wherein the hydrophobic polymer resin is a polyarylate resin having a repeating unit represented by chemical formula (1) shown below, and the number average molecular weight of the polyarylate resin is within a range from 20,000 to 30,000:

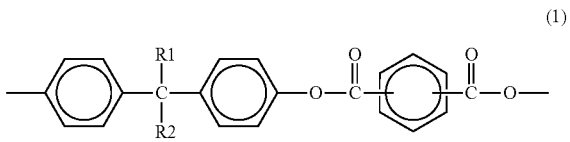

wherein each of R1 and R2 represents a lower alkyl group of 1 to 5 carbon atoms, and R1 and R2 may be identical or different.

2. The adsorbent for removing blood cells according to claim 1, wherein the hydrophobic polymer resin further comprises a polyethersulfone resin having a repeating unit represented by chemical formula (2) or chemical formula (3) shown below:

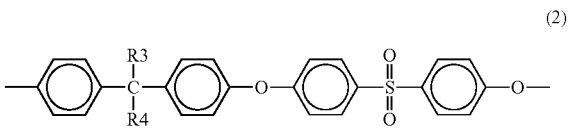

wherein each of R3 and R4 represents a lower alkyl group of 1 to 5 carbon atoms, and R3 and R4 may be identical or different

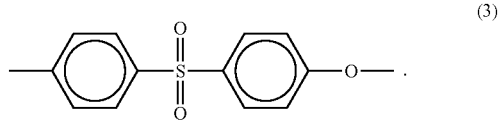

3. The adsorbent for removing blood cells according to claim 2, wherein the number average molecular weight of the polyethersulfone resin is within a range from 15,000 to 30,000.

4. The adsorbent for removing blood cells according to claim 1, wherein the adsorbent has a surface center line average roughness of 5 to 34 nm.

5. The adsorbent for removing blood cells according to claim 1, wherein the adsorbent is in a beads form.

6. The adsorbent for removing blood cells according to claim 1, wherein the adsorbent is in a form of hollow fibers or solid fibers.

* * * * *